United States Patent [19]
Bryant et al.

[11] Patent Number: 5,484,796
[45] Date of Patent: Jan. 16, 1996

[54] NAPHTHYL COMPOUNDS, INTERMEDIATES, PROCESSES, COMPOSITIONS, AND METHOD OF INHIBITING AORTAL SMOOTH MUSCLE CELL PROLIFERATION

[75] Inventors: Henry U. Bryant, Indianapolis; George J. Culliman, Trafalgar; Jeffrey A. Dodge, Indianapolis; Kennan J. Fahey, Indianapolis; Charles D. Jones, Indianapolis; Charles W. Lugar, McCordsville; Brian S. Muehl, Indianapolis, all of Ind.

[73] Assignee: Eli Lilly and Company, Indianapolis, Ind.

[21] Appl. No.: 426,770

[22] Filed: Apr. 21, 1995

Related U.S. Application Data

[62] Division of Ser. No. 309,525, Sep. 20, 1994.

[51] Int. Cl.$^6$ .......... A61K 31/445; C07D 211/06; C07D 211/20
[52] U.S. Cl. .......... 514/319; 514/212; 514/238.8; 514/428; 514/651; 540/609; 544/106; 546/205; 548/576; 564/347
[58] Field of Search .......... 540/609; 544/106; 546/205; 548/576; 564/347; 514/212, 319, 428, 238.8, 651

[56] References Cited

U.S. PATENT DOCUMENTS

| | | | |
|---|---|---|---|
| 3,274,213 | 9/1966 | Lednicer | 546/205 |
| 3,293,263 | 12/1966 | Lednicer | 546/205 |
| 3,313,853 | 4/1967 | Lednicer | 546/205 |
| 3,320,271 | 5/1967 | Lednicer | 260/307 |
| 3,394,125 | 7/1968 | Crenshaw | 548/525 |
| 3,396,169 | 8/1968 | Lednicer | 546/205 |
| 3,413,305 | 11/1968 | Crenshaw | 260/326.5 |
| 3,483,293 | 12/1969 | Duncan et al. | 546/205 |
| 3,567,737 | 3/1971 | Lednicer | 546/205 |
| 3,862,232 | 1/1975 | Lednicer | 564/324 |
| 4,133,814 | 1/1979 | Jones et al. | 546/202 |
| 4,230,862 | 10/1980 | Suarez et al. | 546/237 |
| 4,380,635 | 4/1983 | Peters | 546/202 |
| 4,418,068 | 11/1983 | Jones | 514/320 |
| 5,254,568 | 10/1993 | Kapil et al. | 514/320 |
| 5,384,332 | 1/1995 | Fontana | 514/648 |

FOREIGN PATENT DOCUMENTS

| | | |
|---|---|---|
| 0124369 | 11/1984 | European Pat. Off. . |
| WO93/10113 | 5/1993 | Japan . |
| WO93/1074 | 6/1993 | WIPO . |

OTHER PUBLICATIONS

Crenshaw, R. R., et al., *J. Med. Chem.*, 14(12):1185–1190 (1971).
Durani, N., et al., *Indian J. Chem.*, 22B:489–490 (1983).
Jones, C. D., et al., *J. Med. Chem.*, 35:931–938 (1992).
Cerny, et al., *Tetrahedran Letters*, 8:691–694 (1972).
Lednicer, D., et al., *J. Med. Chem.*, 8:52–57 (1964).
Lednicer, D., et al., *J. Med. Chem.*, 9:172–175 (1965).
Lednicer, D., et al., *J. Med. Chem.*, 10:78–84 (1967).

*Primary Examiner*—Ceila Chang
*Attorney, Agent, or Firm*—Steven A. Fontana

[57] ABSTRACT

The present invention provides a compound of formula I

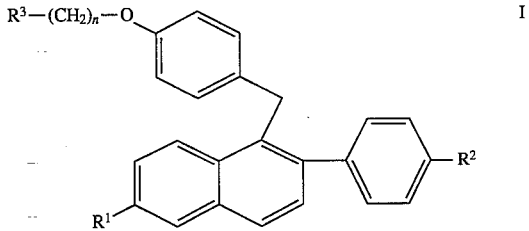

wherein
$R^1$ is —H, —OH, —O($C_1$–$C_4$ alkyl), —OCOC$_6$H$_5$, —OCO($C_1$–$C_6$ alkyl), or —OSO$_2$($C_4$–$C_6$ alkyl);
$R^2$ is —H, —OH, —O($C_1$–$C_4$ alkyl), —OCOC$_6$H$_5$, —OCO($C_1$–$C_6$ alkyl) or —OSO$_2$($C_4$–$C_6$ alkyl);
n is 2 or 3; and
$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof, for inhibiting aortal smooth muscle cell proliferation.

1 Claim, No Drawings

5,484,796

NAPHTHYL COMPOUNDS, INTERMEDIATES, PROCESSES, COMPOSITIONS, AND METHOD OF INHIBITING AORTAL SMOOTH MUSCLE CELL PROLIFERATION

This application is a division of pending prior application Ser. No. 08/309,525, filed on Sep. 20, 1994.

FIELD OF THE INVENTION

This invention related to the fields of pharmaceutical and organic chemistry and provides novel naphthyl compounds which are useful for the treatment of the various medical indications associated with post-menopausal syndrome, and uterine fibroid disease, endometriosis, and aortal smooth muscle cell proliferation. The present invention further relates to intermediate compounds and processes useful for preparing the pharmaceutically active compounds of the present invention, and pharmaceutical compositions.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of mensus. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new naphthalene compounds, pharmaceutical compositions thereof, and methods of using such compounds for the treatment of post-menopausal syndrome and other estrogen-related pathological conditions such as those mentioned below.

Uterine fibrosis (uterine fibroid disease) is an old and ever present clinical problem which goes under a variety of names, including uterine fibroid disease, uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undesirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated causing a mild degree of bone loss with continued therapy. Therefore, new methods of treating endometriosis are desirable.

Smooth aortal muscle cell proliferation plays an important role in diseases such as atherosclerosis and restenosis. Vascular restenosis after percutaneous transluminal coronary angioplasty (PTCA) has been shown to be a tissue response characterized by an early and late phase. The early phase occurring hours to days after PTCA is due to thrombosis with some vasospasms while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology*, 8: 369–375 (August 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., *American Heart Journal*, 122: 171–187 July 1991).

In the pathogenesis of restenosis excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth aortal muscle cells are useful in the treatment and prevention of restenosis. The present invention provides for the use of compounds as smooth aortal muscle cell proliferation inhibitors and, thus inhibitors of restenosis.

SUMMARY OF THE INVENTION

The present invention relates to compounds of formula I

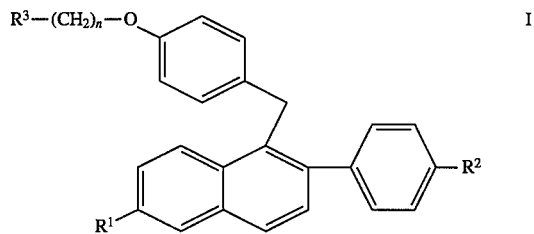

wherein $R^1$ is —H, —OH, —O($C_1$–$C_4$ alkyl), —OCOC$_6$H$_5$, —OCO($C_1$–$C_6$ alkyl), or —OSO$_2$($C_4$–$C_6$ alkyl);

$R^2$ is —H, —OH, —O($C_1$–$C_4$ alkyl), —OCOC$_6$H$_5$, —OCO($C_1$–$C_6$ alkyl), or —OSO$_2$($C_4$–$C_6$ alkyl);

n is 2 or 3; and

R³ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

Also provided by the present invention are intermediate compounds of formula VI which are useful for preparing the pharmaceutically active compounds of the present invention, and are shown below

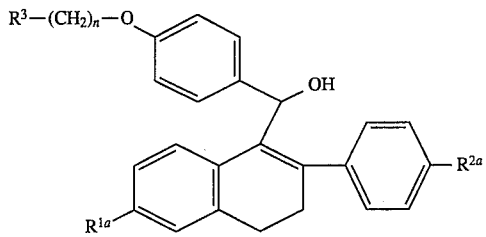

wherein $R^{1a}$ is —H, —OH, or —O(C$_1$–C$_4$ alkyl);

$R^{2a}$ is —H, —OH, or —O(C$_1$–C$_4$ alkyl);

$R^3$, Y, and n are as defined above;

or a pharmaceutically acceptable salt thereof.

The present invention further relates to pharmaceutical compositions containing compounds of formula I, optionally containing estrogen or progestin, and the use of such compounds, alone, or in combination with estrogen or progestin, for alleviating the symptoms of post-menopausal syndrome, particularly osteoporosis, cardiovascular related pathological conditions, and estrogen-dependent cancer. As used herein, the term "estrogen" includes steroidal compounds having estrogenic activity such as, for example, 17β-estradiol, estrone, conjugated estrogen (Premarin®), equine estrogen, 17β-ethynyl estradiol, and the like. As used herein, the term "progestin" includes compounds having progestational activity such as, for example, progesterone, norethylnodrel, nongestrel, megestrol acetate, norethindrone, and the like.

The compounds of the present invention also are useful for inhibiting uterine fibroid disease and endometriosis in women and aortal smooth muscle cell proliferation, particularly restenosis, in humans.

Also provided by the present invention is a process for preparing a compound of formula Ia

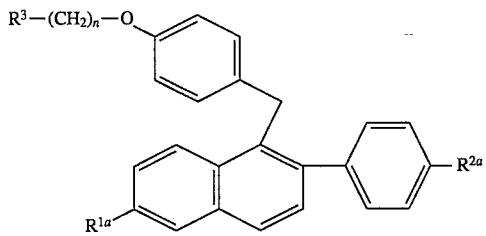

wherein $R^{1a}$ is —H, —OH, or —O(C$_1$–C$_4$ alkyl);

$R^{2a}$ is —H, —OH, or —O(C$_1$–C$_4$ alkyl);

$R^3$ is 1-piperidinyl, 1-pyrrolidinyl, dimethylamino, diethylamino, or 1-hexamethyleneimino; and n is 2 or 3;

or a pharmaceutically acceptable salt thereof, which comprises a) reacting a compound of formula IIId

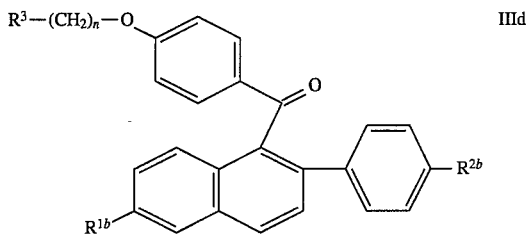

wherein $R^{1a}$ is —H or —O(C$_1$–C$_4$ alkyl);

$R^{2a}$ is —H or —O(C$_1$–C$_4$ alkyl); and $R^3$ and n are as defined above, with a reducing agent in the presence of a solvent having a boiling point in the range from about 150° C. to about 200° C., and heating the mixture to reflux;

b) when $R^{1b}$ and/or $R^{2b}$ is —O(C$_1$–C$_4$ alkyl), optionally removing the $R^{1b}$ and/or $R^{2b}$ hydroxy protecting groups; and c) optionally salifying the reaction product from step a) or b).

DETAILED DESCRIPTION OF THE INVENTION

One aspect of the present invention includes compounds of formula I

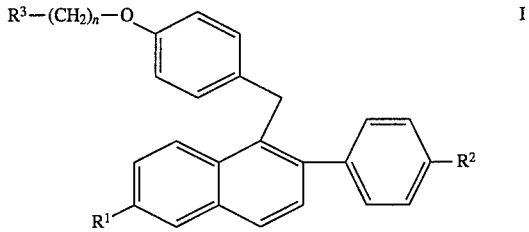

wherein $R^1$ is —H, —OH, —O(C$_1$–C$_4$ alkyl), —OCOC$_6$H$_5$, —OCO(C$_1$–C$_6$ alkyl), or —OSO$_2$(C$_4$–C$_6$ alkyl);

$R^2$ is —H, —OH, —O(C$_1$–C$_4$ alkyl), —OCOC$_6$H$_5$, —OCO(C$_1$–C$_6$ alkyl), or —OSO$_2$(C$_4$–C$_6$ alkyl);

n is 2 or 3; and $R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

General terms used in the description of compounds herein described bear their usual meanings. For example, "C$_1$–C$_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "C$_1$–C$_4$ alkoxy" represents a C$_1$–C$_4$ alkyl group attached through an oxygen such as, for example, methoxy, ethoxy, n-propoxy, isopropoxy, and the like. Of these C$_1$–C$_4$ alkoxy groups, methoxy is highly preferred.

The starting material for one route of preparing compounds of the present invention, compounds of formula II below, are made essentially as described in U.S. Pat. No. 4,230,862, issued Oct. 28, 1980, which is herein incorporated by reference.

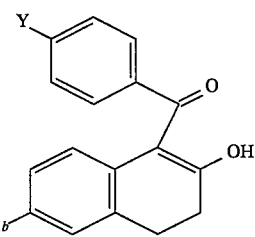

II wherein
R$^{1b}$ is —H or —O(C$_1$-C$_4$ alkyl); and
Y is methoxy or R$^3$—(CH$_2$)$_n$—O—, in which R$^3$ and n are as defined above. Preferably, R$^{1b}$ is methoxy, Y is R$^3$—(CH$_2$)$_n$—O—, R$^3$ is 1-piperidinyl, and n is 2.

In general, a readily available tetralone, or a salt thereof, of the formula

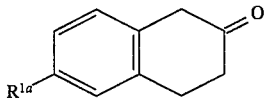

wherein R$^{1a}$ is as defined above, is reacted with an acylating agent such as a phenyl benzoate of the formula

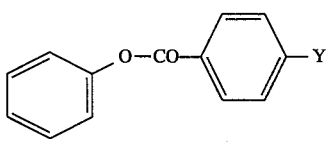

wherein Y is as defined above. The reaction generally is carried out in the presence of a moderately strong base such as sodium amide and is run at ambient temperature or below.

For the next step, one option allows for the selected formula II compound to be reacted, after conversion to an enol phosphate derivative generation in situ, under Grignard reaction conditions, with a Grignard reagent of the formula R$^{2b}$—MgBr wherein R$^{2b}$ is —H or —O(C$_1$-C$_4$ alkyl), to provide compounds of formula IIIa, below, which also are known in the art (see, e.g. U.S. Pat. No. 4,230,862, supra).

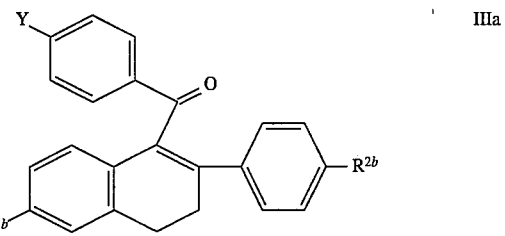

wherein R$^{1b}$, R$^{2b}$, and Y are as defined above, or a pharmaceutically acceptable salt thereof.

When Y of a formula IIIa compound is R$^3$—(CH$_2$)$_n$—O—, such compounds can be reduced or deprotected as described infra. When Y of formula III compounds is methoxy, one of the synthetic routes shown in Scheme I below is first utilized. In Scheme I, R$^{1b}$, R$^{2b}$, R$^3$, and n are as defined above.

Scheme I

A

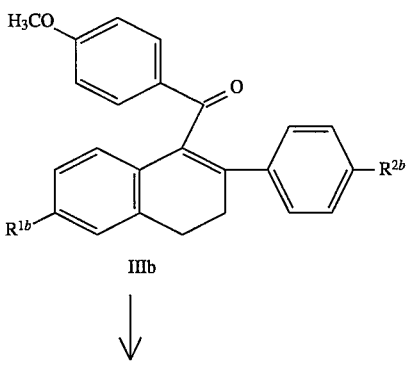

IIIb

↓

B

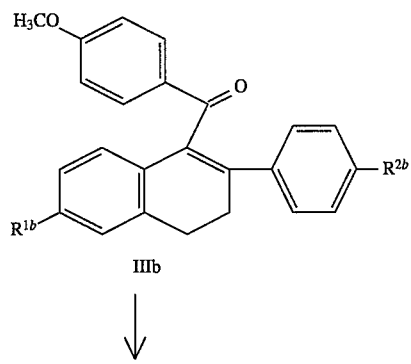

IIIb

↓

-continued
Scheme I

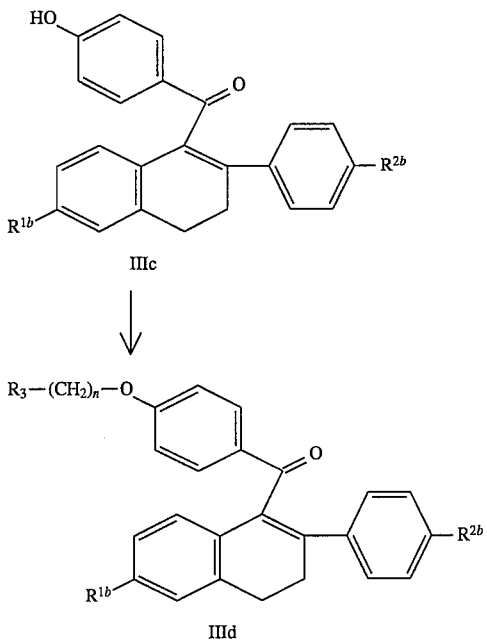

IIIc

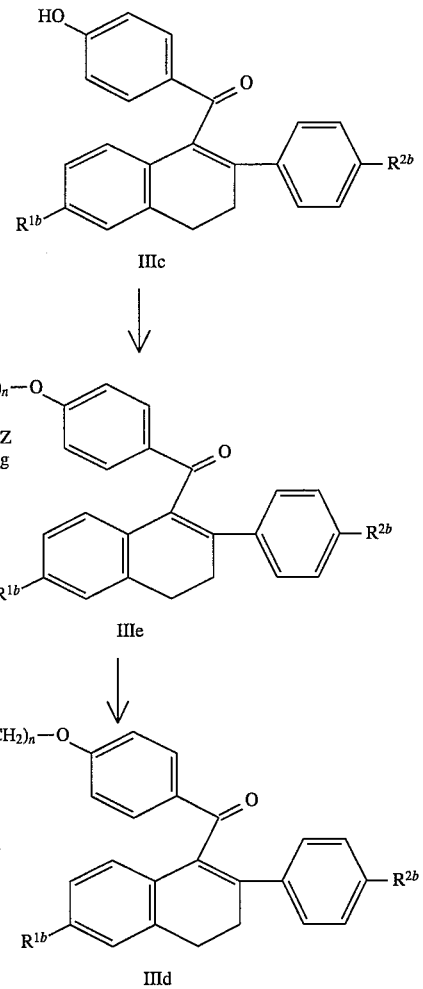

IIIc

↓

R₃—(CH₂)ₙ—O—...

IIId

Z—(CH₂)ₙ—O—...
(in which Z is a leaving group)

IIIe

↓

R³—(CH₂)ₙ—O—...

IIId

Each step of synthetic routes A and B of Scheme I are carried out via procedures well known to one of ordinary skill in the art.

For example, compounds of formula IIIc are prepared by treating formula IIIb compounds with pyridine hydrochloride at reflux. Under these conditions, should $R^{1b}$ and/or $R^{2b}$ be alkoxy, these groups will be dealkylated to hydroxy groups. Using this procedure will eliminate the deprotection step of such alkoxy group (s) at a later stage, if desired.

Alternatively, the Y methoxy group of formula IIIb can selectively be demethylated by treating the compound with an equivalent of sodium thioethoxide in an inert solvent such as N,N-dimethylformamide (DMF) at a moderately elevated temperature of about 80° C. to about 100° C. The process of this step can be monitored via standard chromatographic techniques such as thin layer chromatography (TLC).

Once a formula IIIc compound is prepared, it can be reacted with a compound of the formula

wherein $R^3$ is as defined above and Q is a bromo or, preferably, a chloro moiety, to provide compounds of formula IIId. This reaction is shown as the last step of route A of Scheme I.

Under normal alkylation conditions, this reaction will be effected at each of the hydroxy groups which may be present in a formula IIIc molecule. However, selective alkylation at the 4-hydroxybenzoyl group can be achieved by carrying out the reaction in the presence of an excess of finely powdered potassium carbonate and using an equivalent to slight excess of the Q—(CH₂)—R³ reactant.

To prepare compounds of formula IIIe, as shown in route B of Scheme I, a formula IIIc compound is reacted with an excess of an alkylating agent of the formula

wherein Z and Z' each are the same or different leaving group, in an alkali solution.

Appropriate leaving groups include, for example, the sulfonates such as methanesulfonate, 4-bromosulfonate, toluenesulfonate, ethanesulfonate, isopropanesulfonate, 4-methoxybenzenesulfonate, 4-nitrobenzenesulfonate, 2-chlorobenzene sulfonate, and the like, halogens such as bromo, chloro, iodo, and the like, and other related groups. A preferred alkylating agent is 1,2-dibromoethane, and at least 2 equivalents, preferably, more than 2 equivalents, of 1,2-dibromoethane is used per equivalent of substrate.

A preferred alkali solution for this alkylation reaction contains potassium carbonate in an inert solvent such as, for example, methylethyl ketone (MEK) or DMF. In this solution, the 4-hydroxy group of the benzoyl moiety of a formula IIId compound exists as a phenoxide ion which displaces one of the leaving groups of the alkylating agent.

This reaction is best run when the alkali solution containing the reactants and reagents is brought to reflux and allowed to run to completion. When using MEK as the preferred solvent, reaction times run from about 6 hours to about 20 hours.

The reaction product from this step, a compound of formula IIIe, is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, via standard techniques, to form compounds of formula IIId. Preferably, the hydrochloride salt of piperidine is reacted with the formula IIIe compound in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step can be monitored via standard chromatographic techniques.

Compounds of formula IIId represent the starting material for one process for preparing the pharmaceutically active compounds of formula Ia, as shown in Scheme II below.

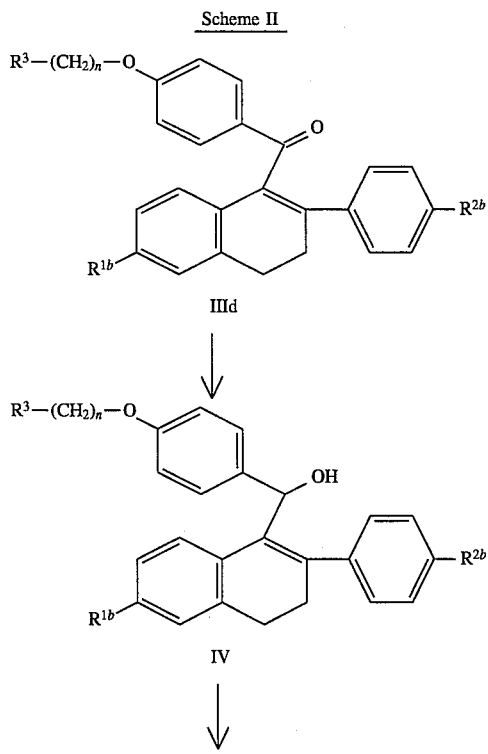

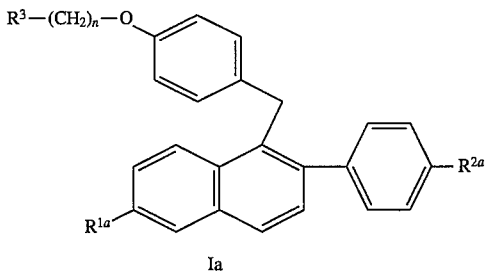

wherein $R^{1a}$, $R^{2a}$, $R^3$, and n are as defined above.

In Scheme II, a formula IIId compound, or a salt thereof, is added to an appropriate solvent and reacted with a reducing agent such as, for example, lithium aluminum hydride (LAH). Although the free base of a formula IIId compound may be used in this reaction, an acid addition salt, preferably the hydrochloride salt, is often more convenient.

The amount of reducing agent used in this reaction is an amount sufficient to reduce the carbonyl group of formula IIId compound to form the novel carbinol compounds of formula IV. Generally, a liberal excess of the reducing agent per equivalent of the substrate is used.

Appropriate solvents include any solvent or mixture of solvents which will remain inert under reducing conditions. Suitable solvents include diethyl ether, dioxane, and tetrahydrofuran (THF). The anhydrous form of these solvents is preferred, and anhydrous THF is especially preferred.

The temperature employed in this step is that which is sufficient to effect completion of the reduction reaction. Ambient temperature, in the range from about 17° C. to about 25° C., generally is adequate.

The length of time for this step is that amount necessary for the reaction to occur. Typically, this reaction takes from about 1 hour to about 20 hours. The optimal time can be determined by monitoring the progress of the reaction via conventional chromatographic techniques.

The carbinol products from this reaction step (formula IV compounds) are extracted essentially via the method described in Example 7, infra, are novel, and are useful for the methods described herein.

Once a carbinol of the present invention is prepared, such a compound is added to an inert solvent such as, for example, ethyl acetate, followed by the addition of a strong protic acid such as hydrochloric acid to provide novel compounds of formula Ia. This reaction typically is run at ambient temperature from about 17° C. to about 25° C., and generally only takes from about a few minutes to about 1 hour to complete. Crystallization of the final product is carried out through standard procedures, essentially as described in Example 1, infra.

Dealkylation/deprotection of terminally-protected hydroxy groups can be carried out prior to the preparation of formula IV compounds, prior to the preparation of formula Ia compounds, or after protected compounds of formula Ia are prepared, via procedures known to one of ordinary skill in the art. It is preferred, however, to dealkylate a protected formula Ia compound after its formation.

The reaction shown in Scheme II provides novel, pharmaceutically active compounds of formula Ia in which $R^{1a}$ and $R^{2a}$ each are hydrogen, hydroxy or $C_1$–$C_4$ alkoxy. Preferred formula Ia compounds are those in which $R^{1a}$ and $R^{2a}$ each are methoxy, or $R^{1a}$ and $R^{2a}$ each are hydroxy, $R^3$ is piperidinyl, and n is 2. These preferred compounds, the latter being especially preferred, as well as other formula Ia compounds, can be used as pharmaceutical agents or can be further derivitized to provide other formula I compounds which also are useful for practicing the methods of the present invention.

As an alternative to the reactions shown in Scheme II, a novel, one-step process may be used to prepare formula Ia compounds of the present invention by reducing a ketone of formula V below. More particularly, when $R^{1a}$ and/or $R^{2a}$ are —O($C_1$-$C_4$ alkyl), these hydroxy protecting groups may be removed prior to using the present novel process, or optionally may be removed, in situ, following the present one-step reduction process. Additionally, the product from this process, which may have 1 or 2 unprotected or protected hydroxy moieties, optionally may be salified via known procedures or as herein described.

In this process, a formula V compound

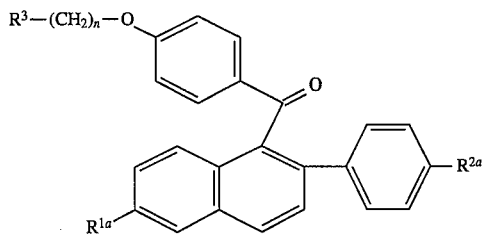

V wherein $R^{1a}$, $R^{1a}$, and n are as defined above, or a salt thereof, is reacted with a reducing agent such as lithium aluminum hydride or Red-Al®[sodium bis(2-methoxyethoxyaluminum hydride)] in the presence of a solvent having a boiling point in the range from about 150° C. to about 200° C.

A compound of formula V is prepared by reacting a compound of formula IIIb (as described above) with about 2 equivalents of 2,3-dichloro-5,6-dicyano-1,4-benzoquinone (DDQ) in the presence of an inert solvent or mixture of solvents such as, for example, dioxane, dichloromethane, toluene, dichloroethane or benzene. The reaction mixture generally is heated to reflux for about 1 to 2 hours, and then allowed to stir at ambient temperature for a period from about 36 to about 72 hours. The resulting compound of formula VI

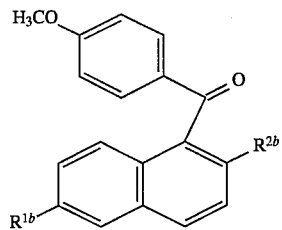

VI wherein $R^{1b}$ and $R^{2b}$ are as defined above, is then demethylated as described above, and alkylated with a compound of the formula $R^2$—$(CH_2)_n$—Q wherein $R^3$ is as defined above, via the above described procedures.

For the present reduction reaction, the amount of reducing agent used in this reaction is an amount sufficient to reduce the carbonyl group of a formula V compound to form a compound of formula Ia. Generally, a liberal excess of the reducing agent per equivalent of the substrate is used.

The solvent used in the process is required to have a relatively high boiling point, in the range from about 150° C. to about 200° C., as represented by solvents such as, for example n-propyl benzene, diglyme (1,1'-oxybis[2-methoxyethane]), and anisole. Of these, n-propyl benzene is the preferred solvent with formula V compounds when $R^{1a}$ and/or $R^{2a}$ is —$OCH_3$ and —$C_6H_4$—4'-C($C_1$-$C_4$ alkyl). Red-Al, used as both a solvent and a reducing agent, is preferred when $R^{1a}$ is —OH and/or $R^{2a}$ is —$C_6H_4$—4'-OH.

The temperature used in this reaction is that which is sufficient to complete the reduction reaction. Preferably, the reaction mixture is heated to reflux for about 15 minutes to about 6 hours, allowed to cool to ambient temperature, and worked up via standard procedures [see, e.g., Fieser and Fieser, *Reagents for Organic Synthesis*, Vol. 1, page 584 (1968)] and as further described in the Examples herein. The optimal amount of time for this reaction to run, typically from about 10 minutes to about 1 hour, can be determined by monitoring the progress of the reaction via standard techniques.

The formula Ia products from the one-step reaction are extracted essentially as described in Example 2, infra. Preferred formula Ia compounds from this reaction are the same as those preferred formula Ia compounds described above, and can be used as pharmaceutically active agents for the methods herein described, or can be derivatized to provide other novel compounds of formula I which also are useful for the present methods.

For example, when $R^{1a}$ and/or $R^{2a}$ of a formula Ia compound are $C_1$-$C_4$ alkyl hydroxy protecting groups (thus, not having been dealkylated as one option in Scheme 1 provides), such as groups can be removed via standard dealkylation techniques, as described in Example 2, infra, to prepare an especially preferred compound of formula Ia.

Other preferred compounds of formula I are prepared by replacing the newly formed $R^{1a}$ and/or $R^{2a}$ hydroxy groups of a formula Ia compound with a moiety of the formula —O—CO—($C_1$-$C_6$ alkyl), or —O—$SO_2$—($C_4$-$C_6$ alkyl) via well known procedures. See, e.g., U.S. Pat. No. 4,358,593.

For example, when an —O—CO($C_1$-$C_6$ alkyl) group is desired, the dihydroxy compound of formula Ia is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The acylation reactions which provide the aforementioned terminal $R^1$ and $R^2$ groups of compounds of formula I are carried out at moderate temperatures in the range from about −25° C. to about 100° C., frequently under an inert atmosphere such as nitrogen gas. However, ambient temperature is usually adequate for the reaction to run.

Such acylations of these hydroxy group also may be performed by acid-catalyzed reactions of the appropriate carboxylic acids in inert organic solvents or heat. Acid catalysts such as sulfuric acid, polyphosphoric acid, methanesulfonic acid, and the like are used.

The aforementioned $R^1$ and/or $R^2$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, e.g., *Bull, Chem. Soc. Japan,* 38:1979 (1965), and *Chem. Ber.,* 788 and 2024 (1970).

Each of the above techniques which provide —O—CO—($C_1$-$C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the $R^{1a}$ and/or $R^{2a}$ group of a formula Ia compound is converted to a group of the formula —O—$SO_2$—($C_4$-$C_6$ alkyl), the formula Ia dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.,* 97: 2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

Collectively, formula Ia compounds with their various defined substituents, and their derivatized compounds as described above, are represented as compounds of formula I of the present invention.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, arcylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous d-6 DMSO was used as the solvent unless otherwise indicated.

PREPARATION 1

[3,4-Dihydro-2-(4-methoxyphenyl)-6-methoxynaphthalen-1-yl](4-methoxyphenyl)methanone

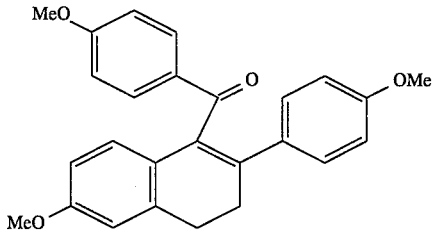

To a suspension of sodium hydride (12.75 g of a 60% oil dispersion pre-washed with hexanes, 0.32 mol) stirring in tetrahydrofuran (THF) (650 mL) at 0° C. was added a solution of (3,4-dihydro-2-hydroxy-6-methoxy-1-naphthylenyl) (4-methoxyphenyl)methanone (90.0 g, 0.29 mmol See, e.g., U.S. Pat. No. 4,230,862) and diphenylchlorophosphate (77.8 g, 0.29 mol) in THF (750 mL). The rate of addition was such that the reaction temperature was maintained below 8° C. After stirring for 3 hours at 0° C., 4-MeOC$_6$H$_4$MgBr (1.5 equivalents of a 0.064 g/mL solution in THF) was added dropwise and the resulting mixture allowed to gradually warm to room temperature. After 12 hours, the solution was quenched by addition of cold aqueous ammonium chloride. The organic portion was separated from the mixture and the aqueous portion extracted with ethyl acetate. The combined organic extracts were dried (sodium sulfate), filtered, and concentrated. To the resulting oil was added acetonitrile (1 L) upon which time a precipitate formed. The solids were removed by filtration and the filtrate concentrated to give an oil which was purified by flash chromatography (silica gel, methylene chloride). The desired product was subsequently purified by crystallization from methanol to provide 96.7 g (83%) of the title compound as a yellow crystalline solid: mp=172°–173° C.; $^1$H-NMR (DMSO-d$_6$) δ 7.75 (d, J=8.7 Hz, 2H), 7.16 (d, J=8.6 Hz, 2H), 6.60–6.90 (complex, 7H), 3.74 (s, 3H), 3.71 (s, 3H), 3.64 (s, 3H), 2.96 (m, 2H), 2.69 (m, 2H); MS (FD) m/e 400 (M+).

PREPARATION 2

[3,4-Dihydro-2-(4-methoxyphenyl)-6-methoxynaphthalen-1-yl](4-hydroxyphenyl)methanone

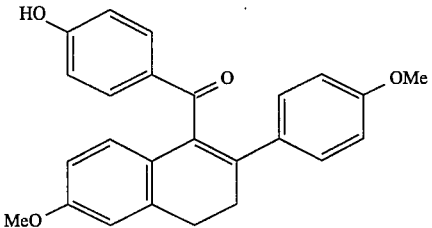

To a solution of lithium ethanethiol [prepared by adding n-BuLi (87.8 mL of a 1.6M solution in hexanes, 140 mmol) to a solution of ethanethiol (12.1 mL, 164 mmol) stirring at 0° C. in ethyl ether (400 mL) followed by brief stirring and concentration] stirring in dimethylformamide (400 mL) was added the product of Preparation 1 (46.7 g, 117 mmol). The mixture was then heated to 100° C. After 1 hour, the reaction was concentrated and the resulting brown oil dissolved in chloroform. This solution was extracted with aqueous ammonium chloride. The aqueous portion was treated with 1N hydrochloric acid until pH 5 was obtained, and subsequently extracted with chloroform. The combined organic extracts were washed with brine, dried (sodium sulfate), filtered, and concentrated. The resulting brown oil was purifed by flash chromatography (silica gel, ethyl acetate/hexanes gradient) to give 30.0 g (66%) of the title product as a yellow oil: $^{1}$H-NMR (300 MHz, CDCl$_3$) δ 7.74 (m, 2H), 7.16 (m, 2H), 6.85 (d, J=8.0 Hz, 1H), 6.77 (s, 1H), 6.65 (m, 5H), 6.11 (s, 1H), 3.78 (s, 3H), 3.69 (s, 3H), 3.00 (m, 2H), 2.77 (m, 2H): $^{13}$C-NMR (75 MHz, CDCl$_3$) δ 201.1, 162.4, 159.7, 159.6, 137.5, 137.2, 134.6, 134.2, 133.3, 130.6, 129.6, 127.6, 127.2, 116.5, 114.7, 114.5, 112.3, 56.2, 56.0, 30.7, 29.6; Anal. Calc'd. for: C, 77.70; H, 5.74. Found: C, 77.46; H, 5.91. MS (FD) m/e 386 (M+); IR (chloroform) 3400.94, 1641.63, 1601,12 cm$^{-1}$.

PREPARATION 3

[3,4-Dihydro-2(4-methoxyphenyl)-6-methoxynaphthalen-1-yl][4-[2-(1-piperidinyl)ethoxy]phenyl]methanone

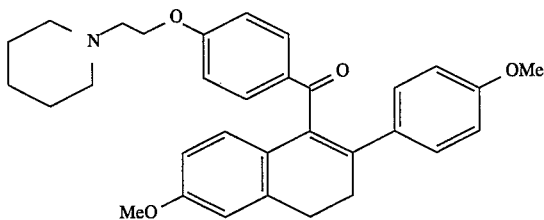

To a solution of the product of Preparation 2 (36 g, 93 mmol) stirring in dimethylformamide (DMF; 1 L) was added potassium iodide (30 mg, 0.18 mmol) followed by potassium carbonate (64.2 g, 465 mmol), and 1-(2-chloroethyl)piperidine monohydrochloride (18.9 g, 102 mmol). The reaction mixture was stirred at ambient temperature overnight then concentrated and the resulting oil dissolved in the chloroform. This solution was washed with thoroughly with water, brine, dried (sodium sulfate), filtered, and concentrated. The resulting oil was purified by flash chromatography (silica gel, methanol/chloroform gradient) to give 43 g (93%) of the title product as a yellow foam: $^{1}$H-NMR (300 MHz, DMSO-d$_6$) δ 7.72 (d, J=8.0 Hz, 1H), 7.15 (d, J=10 Hz, 3H), 6.87 (d, J=11 Hz, 3H), 6.72 (d, J=8 Hz, 2H), 6.62 (s, 2H), 4.05 (m, 2H), 3.69 (s, 3H), 3.63 (s, 3H), 2.95 (m 2H), 2.62 (m, 4H), 2.38 (m, 4H), 1.44 (m, 4H), 1.33 (m, 2H); $^{13}$C-NMR (75 MHz, DMSO-d$_6$) δ 197.2, 168.22, 168.18, 162.5, 162.3, 158.4, 158.3, 136.4, 134.9, 133.0, 133.0, 131.3, 129.6, 128.6, 125.9, 125.4, 114.4, 113.7, 133.6, 113.4, 111.5, 65.7, 62.5, 57.0, 55.0, 55.0, 54.9, 54.1, 29.1, 28.0, 25.4, 23.7; Anal. Calc'd. for: C, 77.24; H, 7.09; N, 2.81. Found: C, 77.44; H, 7.13; N, 2.75. MS (FD) m/e 497 (M+); IR (chloroform) 1672.5 cm$^{-1}$.

EXAMPLE 1

[2-(4-Methoxyphenyl)-6-methoxynaphthalen-1-yl][4-[2-(1-piperidinyl)ethoxy] phenyl]methane hydrochloride

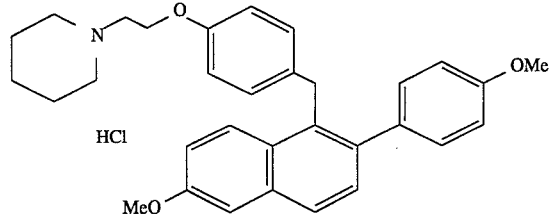

To a solution of lithium aluminum hydride (3.80 g, 94.8 mmol) stirring at 0° C. in dry THF (100 mL) was slowly added a solution of the product of Preparation 3 (23.6 g, 47.4 mmol) in THF (50 mL) over a 45 minute period. The reaction mixture was allowed to stir at ambient temperature overnight for 14 hours, cooled to 0° C., and quenched carefully with water (5 mL). To this solution, sodium hydroxide (15 mL of a 15% w/w aqueous solution) was added dropwise, followed by water (5 mL). The mixture was stirred for 0.5 hours, filtered, and the solids were washed thoroughly with ethyl acetate. The filtrate was then concentrated to give 21 g (89%) of the intermediate product (a carbinol) as a white foam, which was used without further purification. To the intermediate product (23.6 g, 27.4 mmol) stirring at ambient temperature in ethyl acetate (100 mL) was added hydrochloric acid [100 mL of a saturated ethyl acetate solution]. A precipitate immediately formed upon which time the mixture was concentrated. The resulting solid was recrystallized from methanol to give 19.4 g (79%) of the title product as a white crystalline solid: $^{1}$H-NMR (300 MHz, DMSO-d$_6$) δ 10.54 (br s, 1H), 7.72–7.80 (complex, 2H), 7.34–7.38 (complex, 2H), 7.23 (d, J=8.5 Hz, 2H), 7.08 (dd, J=8.4, 2.3 Hz, 1H), 6.80–6.96 (complex, 6H), 4.30 (br s, 4H), 3.85 (s, 3H), 3.76 (s, 3H), 3.37–3.45 (complex, 4H) 3.90–2.99 (m, 2H), 1.61–1.82 (complex, 5H), 1.32–1.39 (m, 1H); MS (FD) m/e 481 (M$^{+}$-hydrochloric acid); Anal. Calc'd. for: C, 74.19; H, 7.00; N, 2.70. Found: C, 74.28; H, 7.18; N, 2.66.

EXAMPLE 3

[2-(4-Benzoyloxyphenyl)-6-benzoyloxynaphthalen-1-yl][4-[2-(1-piperidinyl)ethoxy] phenyl]methane

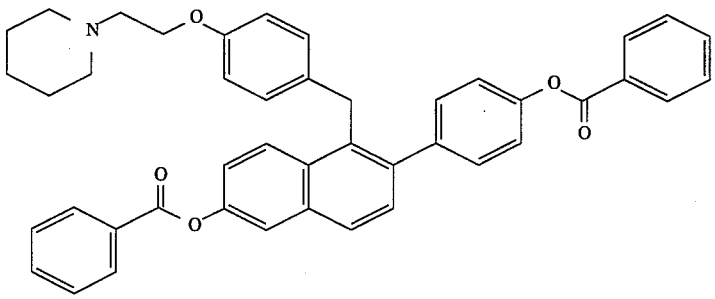

6.75–6.91 (complex, 6H), 4.28–4.31 (complex, 4H), 3.34–3.45 (complex, 4H), 2.95 (m, 1H), 1.63–1.75 (complex, 5H), 1.35 (m, 1H); MS (FD) m/e 454 (M$^+$-hydrochloric acid); Anal. Calc'd. for: C, 73.53; H, 6.58; N, 2.86. Found: C, 73.48; H, 6.57; N, 3.01.

To a suspension of the product of Example 2 (4.1 g, 8.4 mmol) stirring in THF (200 mL) was added N,N-dimethylaminopyridine (10 mg, catalytic). The mixture was cooled to 0° C. and triethylamine (8.5 g, 83.7 mmol) was added. After 10 minutes, benzoyl chloride (4.7 g, 33.5 mmol) was added dropwise and the solution allowed to stir for 60 hours. The precipitate was then filtered off and the filtrate concentrated. Purification of this material by preparatory HPLC (chloroform to 25% ethyl acetate in chloroform gradient) followed by recrystallization from methanol gave 3.78 g of the title compound as a white powder: $^1$H-NMR (300 MHz, DMSO-d$_6$) δ 8.18 (app t, J=9.1 Hz, 4H), 7.91–8.05 (complex, 3H), 7.75 (m, 1H), 7.61–7.69 (m complex, 2H), 7.58 (d, J=8.90 Hz, 1H), 7.43–7.50 (complex, 3H), 7.38 (d, J=8.3 Hz, 2H), 6.91 (d, J=8.5 Hz, 2H), 6.80 (d, J=8.5 Hz, 2H), 4.40 (s, 2H), 3.97 (t, J=3.5 Hz, 2H), 2.60 (t, J=3.3 Hz, 2H), 2.39 (complex, 4H), 1.31–1.52 (complex, 6H); MS (FD) m/e 661 (M$^+$); Anal. Calc'd. for: C, 79.86; H, 5.94; N, 2.12. Found: C, 79.59; H, 6.05; N, 1.96.

EXAMPLE 2

[2-(4-Hydroxyphenyl)-6-hydroxynaphthalen-1-yl][4-[2-(1-piperidinyl)ethoxy]phenyl] methane hydrochloride

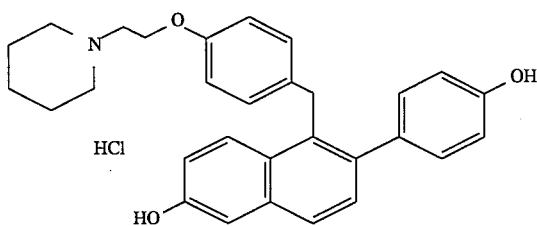

To a solution of the product from Example 1 (5.0 g, 9.6 mmol) stirring in 1,2-dichloroethane (50 mL) at room temperature was added boron trichloride (20 mL, 234 mmol). The resulting dark purple reaction was allowed to stir at ambient temperature overnight then cooled to 0° C. Methanol (50 mL) was then carefully added dropwise over a 2 hours period (caution: gas evolution) upon which time a precipitate formed. The solid was filtered, washed with cold methanol and then with diethyl ether. Recrystallization from methanol gave the title product as a white powder: $^1$H-NMR (300 MHz, DMSO-d$_6$) δ 10.38 (br s, 0.5 H), 9.74 (s, 1H), 9.52 (s, 1H), 7.61–7.68 (complex, 2H), 7.28 (d, J=8.3 Hz, 1H), 7.08–7.14 (complex, 3H), 6.99 (dd, J=9.1, 2.4 Hz, 1H),

EXAMPLE 4

[2-(4-Pivaloyloxyphenyl)-6-pivaloyloxynaphthalen-1-yl] [4-[2-(1-piperdinyl)ethoxy]phenyl]methane

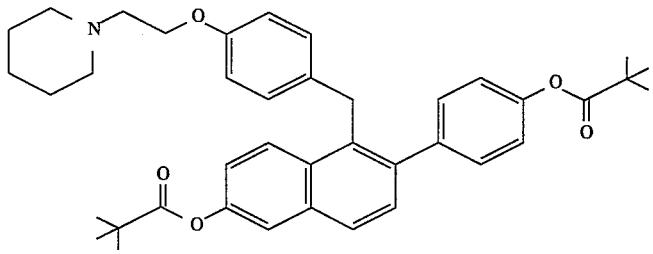

To a suspension of the product of Example 2 (0.250 g, 0.510 mmol) stirring in THF (25 ml) was added N,N-dimethylaminopyridine (2 mg) followed by triethylamine (0.78 mL, 5.6 mmol) and trimethylacetyl chloride (0.25 mL, 2.0 mmol). The resulting mixture was stirred at ambient temperature for 2 hours then poured into ethyl acetate/water (100 mL, 1:1 v/v). The organic layer was separated and the aqueous portion was extracted with ethyl acetate (50 mL). The combined organic extracts were washed with saturated aqueous ammonium chloride (1× 25 mL), saturated aqueous sodium bicarbonate (2×25 mL), and brine (1×25 mL). Purification by radial chromatography (silica gel, 2 mm, 10:8:1:1 ethyl acetate: hexanes: triethylamine: methanol) gave 0.268 g. of the title compound (85%) as a thick oil: IR (chloroform) 2977, 2939, 1746, 1510, 1167, 1146, 1122 cm$^{-1}$; $^1$H NMR (300 MHz, CDCl$_3$) δ 7.87–7.90 (d, 1H, J=9.3 Hz), 7.75–7.78 (d, 1H, J=8.6 Hz), 7.56–7.57 (d, 1H, J=2.4 Hz), 7.43–7.46 (d, 1H, J=8.4 Hz), 7.28–7.31 (m, 3H), 7.10–7.14 (dd, 1H, J=9.2 Hz, J=2.4 Hz), 7.03–7.06 (m, 2H), 6.86–6.88 (d, 2H, J=8.5 Hz), 6.71–6.74 (m, 2H), 4.34 (s, 2H), 4.10–4.15 (m, 2H), 2.79–2.83 (m, 2H), 2.52–2.57 (m, 4H), 1.65–1.68 (m, 4H), 1.45–1.51 (m, 2H), 1.39 (s, 9H), 1.36 (s, 9H); MS (FD) m/e 621 (M+).

EXAMPLE 5

[2-(4-n-Butylsulfonyloxyphenyl)-6-n-butylsulfonyloxynaphthalen-1-yl][4-[2-(1-piperdinyl)ethoxy] phenyl]methane

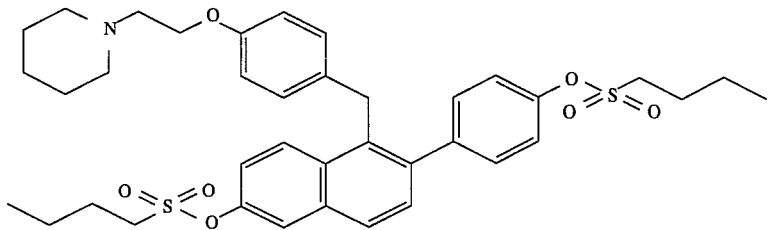

To a suspension of the product of Example 2 (0.250 g, 0.510 mmol) stirring in THF (25 mL) was added, in turn, N,N-dimethylaminopyridine (2 mg), triethylamine (0.78 mL, 5.6 mmol), and butanesulfonyl chloride (0.26 mL, 2.04 mmol). The reaction mixture was stirred at ambient temperature for 2 hours then poured into ethyl acetate/water (100 mL, 1:1) and the organic layer subsequently separated. The aqueous portion was extracted with ethyl acetate (50 mL), and the combined organic layers washed with saturated aqueous ammonium chloride (1×25 mL), followed by saturated aqueous sodium bicarbonate (2×25 mL) and brine (1×25 mL). Purification by radial chromatography (silica gal, 2 mm, 10:8:1:1 ethyl acetate: hexanes: triethylamine: methanol) gave 0.289 g (82%) of the title compound as a thick syrup: IR (chloroform) 3032, 2966, 2940, 2879, 1609, 1510, 1375, 1245, 1171, 1149, 1129, 870, 839 cm$^{-1}$; $^1$H NMR (300 MHz, CDCl$_3$) δ 7.92–7.95 (d, 1H, J=9.3 Hz), 7.81– 7.84 (d, 1H, J=8.6 Hz), 7.77–7.78 (d, 1H, J=2.5 Hz), 7.46– 7.49 (d, 1H, J=8.4 Hz), 7.24–7.34 (m, 5H), 6.84–6.87 (d, 2H, J= 8.6 Hz), 6.74–6.77 (d, 2H, J=8.6 Hz), 4.33 (s, 2H), 4.05– 4.09 (m, 2H), 3.25–3.32 (m, 4H), 2.76–2.81 (m, 2H), 2.48–2.52 (m, 4H), 1.93–2.06 (m, 4H), 1.44–1.61 (m, 10H), 0.96–1.01 (m, 3H); MS (FD) m/e 694 (M+).

EXAMPLE 6

[2-(4-n-hexylsulfonyloxyphenyl)-6-n-hexylsulfonlyoxynaphthalen-1-yl][4-[2-(1-piperdinyl)ethoxy] phenyl]methane

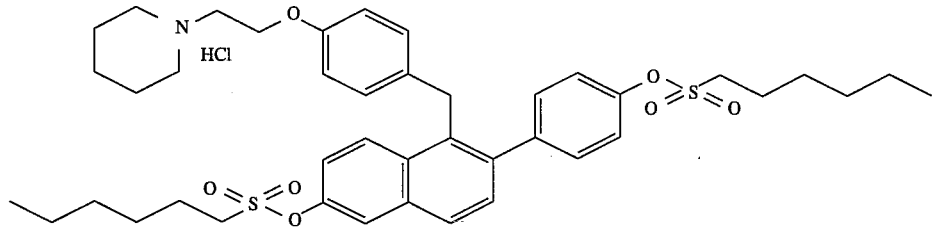

To a solution of the product of Example 2 (0.49 g, 1.00 mmol) stirring in THF (200 mL) at ambient temperature were sequentially added N,N-dimethylformamide (10 mg), triethylamine (0.50 g, 5 mmol), and hexylsulfonyl chloride (0.46 g, 2.5 mmol). After 18 hours, the reaction mixture was concentrated and the resulting dark oil partitioned between ethyl acetate and a saturated aqueous solution of sodium bicarbonate. The organic extract was separated, dried (sodium sulfate), and concentrated. The crude material was dissolved in ethyl acetate and ethereal hydrochloric acid added (10 mL of a saturated solution). The resulting precipitate was triturated with Et$_2$O and dried to give 1.2 g of the desired product as a thick, gummy solid: $^1$H NMR (300 MHz, CDCl$_3$) consistent with structure; MS (FD) m/e 938 (M$^+$-hydrochloric acid).

PREPARATION 4

[3,4-Dihydro-2-phenyl-6-methoxynaphthalen-1-yl](4-hydroxyphenyl)methanone

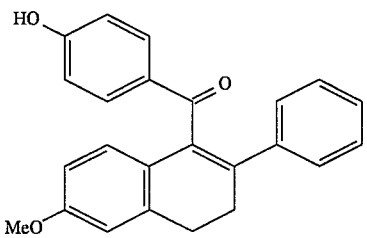

To a solution of lithium ethanethiol [prepared by adding n-BuLi (63.7 ml of a 1.6M solution on hexanes, 101.4 mmol) to a solution of ethanethiol (101.4 mmol) stirring at 0° C. in $Et_2O$ (400 mL) followed by concentration] stirring in dimethylformamide (400 mL) was added (3,4-dihydro-6-methoxy-2-phenyl- 1-naphthalenyl) (4-methoxyphenyl)methanone, prepared as described in Jones, et al., *J. Med. Chem.*, 53:931–938 (1992), supra, (30.0 g, 78.0 mmol) The mixture was then heated to 85° C. After 0.5 hours, the mixture was concentrated and the resulting brown solid dissolved in chloroform. This solution was extracted with saturated aqueous ammonium chloride. The aqueous portion was treated with 1N hydrochloric acid until pH 5 was obtained, and was subsequently extracted with chloroform. The combined organic extracts were washed with brine, dried (sodium sulfate), filtered, and concentrated. The resulting brown oil was purified by flash chromatography (silica gel, ethyl acetate/hexanes gradient) to give 24.7 g (87%) of the desired product as a yellow foam: $^1$H-NMR (300 MHz, $CDCl_3$) δ 7.74 (d, J=8.6 Hz, 2H), 7.15–7.18 (m, 2H), 7.05–7.18 (m, 3H), 6.86 (d, J=8.6 Hz, 1H), 6.78 (d, J=2.7 Hz, 1H), 6.60–6.70 (m, 3H), 6.23 (br s, 1H), 3.78 (s, 3H), 2.95–3.05 (m, 2H), 2.75– 2.85 (m, 2H); Anal. Calc'd. for: C, 80.87; H, 5.66. Found: C, 80.66; H, 5.48; MS (FD) m/e 354 (M+).

PREPARATION 5

[3,4-Dihydro-2-phenyl-6-methoxynaphthalen-1-yl][4-[2-(1-piperdinyl)ethoxy] phenyl]methanone

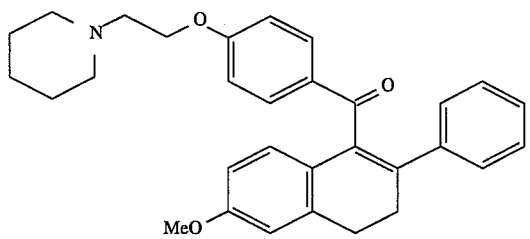

To a solution of the product of Preparation 4 (20.4 g, 57.0 mmol, stirring in dimethylformamide (400 mL) at ambient temperature was added potassium iodide (30 mg, 0.18 mmol) followed by potassium carbonate (39.3 g, 285 mmol) and 1-(2-chloroethylpiperidine monohydrochloride (11.6 g, 62.7 mmol). After 16 hours, the reaction mixture was concentrated and the resulting oil dissolved in chloroform. This solution was washed thoroughly with water, brine, dried (sodium sulfate), filtered and concentrated. The resulting oil was purified by flash chromatography (silica gel, methanol/chloroform gradient) to give 25.1 g (94%) of the desired product as a brown oil: $^1$H-NMR (300 MHz, $CDCl_3$) δ 7.79 (d, J=8.7 Hz, 2H), 7.20–7.33 (m, 2H), 7.04–7.20 (m, 3H), 6.88 (d, J=8.5 Hz, 1H), 6.70–6.82 (m, 3H), 6.62 (m, 1H), 4.08 (t, J=6.0 Hz, 2H), 3.70 (s, 3H), 3.03 (t, J= 7.5 Hz, 2H), 2.70–2.90 (m, 4H), 2.40–2.60 (m, 4H), 1.55–1.65 (m, 4H), 1.40–1.52 (m, 2H); $^{13}$C-NMR (75 MHz, $CDCl_3$) δ 198.33, 162.84, 158.97, 141.21, 136.71, 135.97, 137.78, 131.79, 130.44, 128.08, 127.48, 127.24, 126.59, 126.49, 114.17, 113.80, 111.37, 66.15, 57.68, 55.23, 55.05, 29.73, 28.80, 25.89, 24.12; Anal. Calc'd. for: C, 79.63; H, 7.11; N, 2.99. Found: C, 79.92; H, 7.15; N, 3.07; MS (FD) m/e 467 (M+).

PREPARATION 6

[3,4-Dihydro-2-phenyl-6-methoxynaphthalen-1-yl][4-[2-(1-pyrrolidinyl)ethoxy] phenyl]methanone

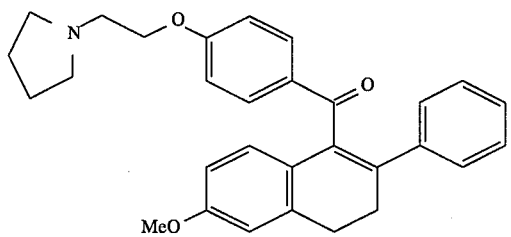

Reaction of the product of Preparation 4 (1.9 g, 5.3 mmol), 1-( 2-chloroethyl)pyrrolidine monohydrochloride (0.99 g, 5.8 mmol), and potassium carbonate (3.65 g, 29.1 mmol) in dimethylformamide (50 mL) according to the procedure in Preparation 5 gave a 81% yield of the title compound as a thick oil: $^1$H-NMR (300 MHz, $CDCl_3$) δ 7.79 (d, J=7.8 Hz, 2H), 7.20–7.30 (m, 2H), 7.05–7.20 (m, 3H), 6.87 (d, J=8.6 Hz, 1H), 6.73–6.84 (m, 3H), 6.60 (d, J= 8.6 Hz, 1H), 4.08 (t, J=5.8 Hz, 2H), 3.78 (s, 3H), 3.00 (t, J=8.0 Hz, 2H), 2.76–2.96 (m, 4H), 2.50–2.70 (m, 4H), 1.75–1.85 (m, 4H); MS (FD) m/e 453 (M+).

EXAMPLE 7

[3,4-Dihydro-2-phenyl-6-methoxynaphthalen-1-yl][4-[2-(1-pyrrolidinyl)ethoxy] phenyl]methanol

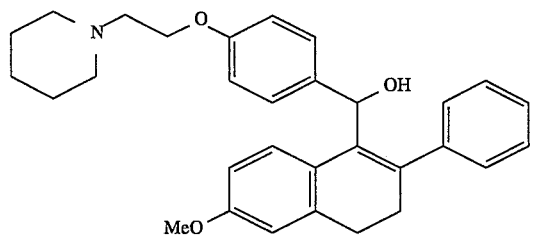

To a suspension of lithium aluminum hydride (1.60 g, 42.8 mmol) stirring at 0° C. in dry THF (200 mL) was added a solution of the product of Preparation 5 (10.0 g, 21.4 mmol) in THF (125 mL) dropwise over a 5 min period. The reaction mixture was allowed to be warmed to ambient temperature and subsequently stirred for 1 hour. The solution was then cooled to 0° C. and quenched carefully with water (1.6 mL). To this solution, sodium hydroxide (4.8 mL of 15% w/w aqueous solution) was added dropwise, followed by water (1.6 mL). After stirring for 30 minutes, the mixture was filtered and the solids washed thoroughly with THF. The filtrate was then concentrated to give 8.7 g (87%) of the desired product as a yellow oil which was used without further purification: $^1$H-NMR (300 MHz, CDCl$_3$) δ 7.20–7.45 (m, 7H), 6.82 (d, J=8.3 Hz, 2H), 6.71 (s, 1H), 6.53 (m, 1H), 5.83 (br s, 1H), 4.07 (t, J=6.1 Hz, 2H), 3.75 (s, 3H), 2.91 (t, J=6.1 Hz, 2H), 2.60–2.80 (m, 4H), 2.40–2.60 (m, 4H), 1.80–1.95 m, 2H), 1.52–1.70 (m, 4H), 1.43 (s, 1H); MS (FD) m/e 469 (M+).

EXAMPLE 8

[3,4-Dihydro-2-phenyl-6-methoxynaphthalen-1-yl][4-[2-(1-pyrrololidinyl)ethoxy] phenyl]methanol Reaction of the product of Preparation 4 (1.8 g, 4.0 mmol), lithium aluminum hydride (0.31 g, 8.0 mmol) in THF (65 mL) according to the preparation of the product of Example 7 gave a 87% yield of the title compound as a white foam: $^1$H-NMR (300 MHz, CDCl$_3$) δ 7.20–7.40 (m, 7H), 6.84 (d, J=8.6 Hz, 2H), 6.71 (s, 1H), 6.51 (m, 1H), 5.83 (d, J=4.9 Hz, 1H), 4.07 (t, J= 6.3 Hz, 2H), 3.75 (s, 3H), 2.82–2.95 (m, 4H), 2.55–2.73 (m, 6H), 2.27 (d, J=3.8 Hz, 1H), 1.70–1.90 (m, 4H), 1.67 (s, 1H); MS (FD) m/e 455 (M+); HRMS FAB+ for C$_{30}$H$_{33}$NO$_3$ calculated 456.2539, found 456.2531.

EXAMPLE 9

[2-Phenyl-6-methoxynaphthalen-1-yl][4-[2-(1-piperdinyl)ethoxy] phenyl]methane hydrochloride

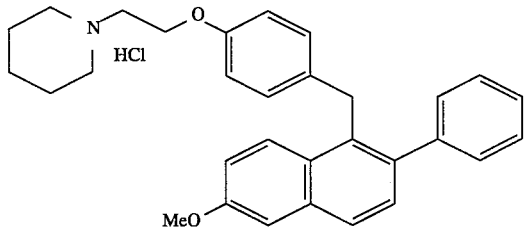

To a solution of the product of Example 7 (8.7 g, 18.5 mmol) stirring in ethyl acetate (100 mL) was added a saturated solution of hydrochloric acid gas in ethyl acetate (250 mL). After 0.5 min, the resulting solution was concentrated to give 8.0 g (89%) of the desired product as a white foam which was used without further purification: $^1$H-NMR (300 MHz, DMSO) δ 7.70–7.85 (m, 4H), 7.30–7.50 (m, 7H), 7.10 (s, 1H), 6.80–7.00 (m, 2H) 4.25–4.40 (m, 4H), 4.00–4.20 (br s, 3H), 3.35–3.55 (m, 4H), 2.85–3.55 (m, 2H), 1.70–1.90 (m, 4H), 1.30–1.45 (m,2H); Anal. Calc'd for: C, 76.29; H, 7.02; N, 2.87. Found: C, 76.56; H, 7.18; N, 2.91; MS (FD) m/e 452 (M+-hydrochloric acid).

EXAMPLE 10

[2-Phenyl-6-methoxynaphthalen-1-yl][4-[2-(1-pyrrolidinyl)ethoxy] phenyl]methane hydrochloride

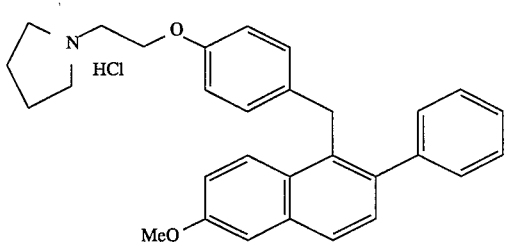

Reaction of the (1.57 g, 3.4 mmol) with ethyl acetate/hydrochloric acid according to the procedure in Example 9 gave a quantitative yield of the title product: $^1$H-NMR 300 MHz, DMSO) δ 7.72–7.85 (m, 2H), 7.28–7.45 (m, 7H), 7.10 (m, 1H), 6.78–6.95 (m, 4H), 4.30 (s, 2H), 4.20–4.25 (m, 2H), 3.84 (s, 3H), 3.40– 3.60 (m, 2H), 2.95–3.10 (m, 2H), 1.80–2.02 (m, 6H); MS (FD) m/e 437 (M+-hydrochloric acid); Anal. Calc'd. for: C, 76.01; H, 6.80; N, 2.95. Found: C, 75.71; H, 6.35; N, 2.32.

EXAMPLE 11

[2-Phenyl-6-hydroxynaphthalen-1-yl][4-[2-(1-piperdinyl)ethoxy] phenyl]methane

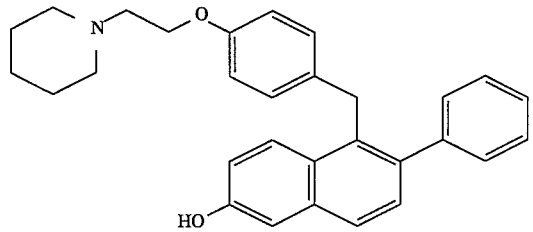

To a solution of the product of Example 9 (4.0 g, 8.0 mmol) stirring in 1,2-dichloroethane (50 mL) at 0° C. was added boron trichloride (10 mL, 117.0 mmol). The resulting dark purple solution was stirred at room temperature overnight in a sealed tube then cooled to 0° C. Methanol (50 mL) was carefully added dropwise over a 30 minute period (caution: gas evolution). The resulting solution was concentrated and dissolved in ethyl acetate. The organic extract was washed with saturated aqueous sodium bicarbonate, brine, dried (sodium sulfate), filtered, and concentrated. The resulting brown foam was purified by flash chromatography (silica gel, methanol/chloroform gradient) to give 2.7 g (63%) of desired product as a white foam: $^1$H-NMR 300 MHz, DMSO) δ 9.72 (br s, 1H), 7.62–7.80 (m, 2H), 7.22–7.50 (m, 6H), 7.10–7.22 (m, 2H), 7.00 (m, 1H), 6.80–6.90 (m, 2H), 6.78 (m, 1H), 4.23 (s, 2H), 3.85–4.10 (m, 2H), 2.50–2.75 (m, 2H), 2.25–2.50 (m, 4H), 1.25–1.56 (m, 6H); Anal. Calc'd. for: C, 82.35; H, 7.14; N, 3.20. Found: C, 82.17; H, 7.11; N, 3.35; MS (FD) m/e 437 (M+); IR (KBr) 2935.07, 2855.01, 1621.38, 1597.26 cm$^{-1}$.

EXAMPLE 12

[2-Phenyl-6-hydroxynaphthalen-1-yl][4-[2-(1-pyrrolidinyl)ethoxy] phenyl]methanol

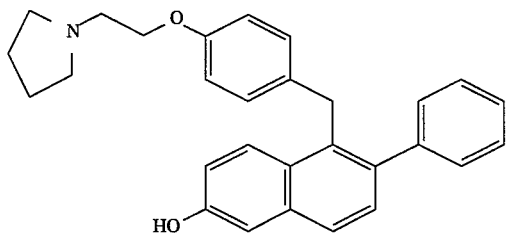

Reaction of the product of Example 10 (1.27 g, 2.7 mmol) with boron trichloride (10 mL, 117 mmol) in 1,2-dichloroethane (30 mL) according to the procedure in Example 11 gave a 32% yield of the desired product as a white solid: IR (KBr) 2932.17, 2876.23, 2815.47, 1620.41, 1597.26 cm$^{-1}$; $^1$H-NMR (300 MHz CDCl$_3$) δ 7.74 (d, J=8,5 Hz, 1H), 7.61 (d, J=8.5 Hz, 1H), 7.20–7.40 (m, 7H), 7.13 (s, 1H), 7.00 (m, 1H), 6.85 (d, J=8.3 Hz, 2H), 6.66 (d, J= 8.3 Hz, 2H), 4.31 (s, 2H), 4.06 (t, J=5.9 Hz, 2H), 2.95 (t, J=5.8 Hz, 2H), 2.65–2.80 (m, 4H), 1.77–1.90 (m, 4H); MS (FD) m/e 424 (M+); Anal. Calc'd. for: C, 82.24; H, 6.90; N, 3.31. Found: C, 82.01; H, 6.84; N, 3.37.

EXAMPLE 13

[3,4-Dihydro-2-(4-methoxyphenyl)-naphthalen-2-yl][4-[2-(1-piperdinylethoxy]phenyl]methanol

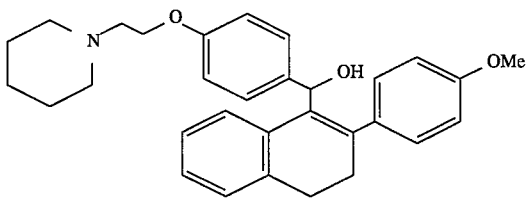

To a suspension of [2-(4-methoxyphenyl)-3,4-dihydronaphth-1-yl] [4-2-(1-piperidenyl)ethoxy]phenyl]methanone mesylate [Jones, et al., *J. Med. Chem.* 35:931 (1992), supra] (2.00 g, 3.35 mmol) stirring in THF 100 mL) at ambient temperature was slowly added lithium aluminum hydride (1.0 g, 26 mmol) over a 20 minute period. After 13 hours, the solution was concentrated to near dryness then carefully quenched with water (50 mL). The resulting mixture was extracted with ethyl acetate (3×100 mL). The combined organic extracts were washed with water, dried (sodium sulfate), and concentrated. Purification by liquid chromatography (Waters Prep 500, silica gel, gradient chloroform to 25% chloroform-methanol) gave 1.0 g of the desired product as a tan amorphous powder: $^1$H-NMR (300 MHz, CDCl$_3$) consistent with structure; MS (FD) m/e 469 (M+).

EXAMPLE 14

[3,4-Dihydro-2-(4-methoxyphenyl)naphthalen-1-yl][4-[2-(1-pyrrolidinyl)ethoxy]phenyl]methanol

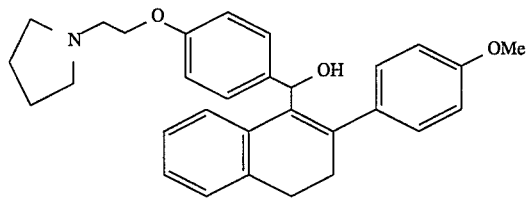

Reaction of [2-(4-methoxyphenyl)-3,5-dihydronaphth-1-yl] [4-2-(1-pyrrolidinyl)ethoxy] phenyl] methanone mesylate [Jones, et al., *J. Med. Chem.* 35:931 (1992), supra] (0.85 g, 1.9 mmol) and lithium aluminum hydride (0.16 g, 4.0 mmol) in THF (150 mL) according to the experimental procedure for Experiment 13 gave 670 mg of the desired compound as a tan amorphous solid: $^1$H-NMR (CDCl$_3$, 300 MHz) consistent with structure; MS (FD) m/e 455 (M+); Anal. Calc'd for: C, 79.20; H, 7.26; N, 3.08. Found: C, 79.11; H, 7.47; N, 2.93.

EXAMPLE 15

[2-(4-Methoxyphenyl)-naphthalen-1-yl][4-[2-(1-piperdinyl)ethoxy] phenyl]methane hydrochloride

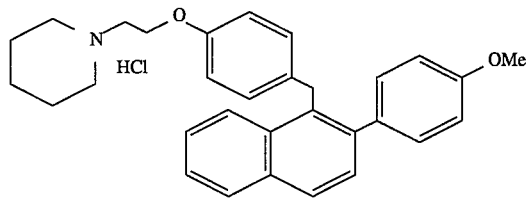

To a solution of the product of Example 13 (1.90 g, 4.21 mmol) stirring in methanol (40 mL) at ambient temperature was added methanolic hydrochloric acid (10 mL of a saturated solution). After 48 hours, the reaction mixture was concentrated and dried. Trituration with ether followed by filtration and drying gave 580 mg of the desired compound as a white powder: $^1$H-NMR (CDCl$_3$, 300 MHz) consistent with structure; MS (FD) m/e 451 (M$^+$-hydrochloric acid).

EXAMPLE 16

[2-(4-Methoxyphenyl)-naphthalen-1-yl][4-[2-(1-pyrrolidinyl)ethoxy] phenyl]methane hydrochloride

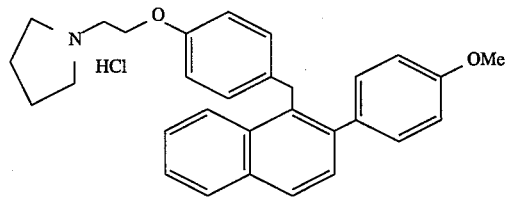

To a solution of the product of Example 14 (2.0 g, 4.58 mmol) stirring in methanol (50 mL) at ambient temperature was added methanolic hydrochloric acid (10 mL of a saturated solution). The reaction mixture was then concentrated to 20 mL and cooled to −20° C. for several hours. Filtration gave 0.62 g of the desired product as a white powder: ¹H-NMR (CDCl₃, 300 MHz) consistent with structure; MS (FD) m/e 437 M⁺-hydrochloric acid); Anal. Calc'd. for: C, 76.01; H, 6.80; N, 2.96. Found: C, 75.95; H, 6.76; N, 2.98.

PREPARATION 7

[3,4-Dihydro-2-(4-methoxyphenyl-6-methoxynaphthalen-1-yl]
[4-[2-(1-pyrrolidinyl)ethoxy]phenyl]methanone

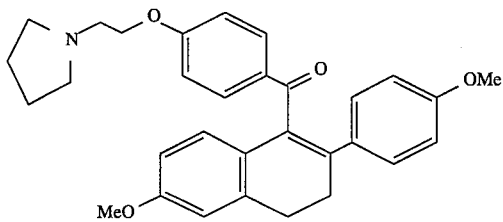

To a solution of the product of Preparation 2 (2.0 g, 5.2 mmol) stirring in dimethylformamide (50 mL) was added potassium carbonate (3.6 g, 26 mmol) and 1-(2-chloroethyl)pyrrolidine monohydrochloride (0.8 g, 5.7 mmol). The reaction mixture was stirred overnight at ambient temperature and concentrated. The resulting oil was dissolved in chloroform and the resulting solution washed thoroughly with water, brine, dried (sodium sulfate), filtered and concentrated. The resulting oil was purified by flash chromatography (silica gel, methanol/chloroform gradient) to give 2.25 g (90% of the desired product as a brown oil: ¹H NMR (300 MHz, CDCl₃) δ 7.80 (d, J=9.4 Hz, 2H), 7.18 (d, J=6.8 Hz, 2H), 6.87 (d, J=8.6 Hz, 2H), 6.65– 6.85 (m, 4H), 6.60 (m, 1H), 4.09 (t, J=5.8 Hz, 2H), 3.78 (s, 3H), 3.71 (s, 3H), 3.01 (t, J=7.5 Hz, 2H), 2.88 (t, J=5.8 Hz, 2H), 2.65–2.85 (m, 2H), 2.60–2.75 (m, 4H), 1.80–1.90 (m, 4H); MS (FD) m/e 483 (M+).

EXAMPLE 17

[3,4-Dihydro-2-(4-methoxyphenyl-6-methoxynaphthalen-1-yl]
[4-[2-(1-pyrrolidinyl)ethoxy]phenyl]methanol

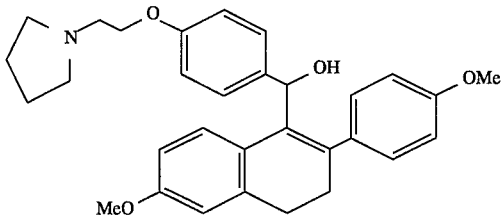

To a suspension of lithium aluminum hydride (0.34 g, 8.80 mmol) stirring at 0° C. in THF (40 mL) was slowly added a solution of the product of Preparation 7 (2.14 g, 4.4 mmol) in THF (25 mL) over a 5 minute period. The reaction mixture was warmed to ambient temperature. After 1 hours, the mixture was cooled to 0° C., and quenched carefully with water (0.4 mL). To this solution, sodium hydroxide (1.2 mL of 15% w/w aqueous solution) was added dropwise, followed by water (0.4 mL). After stirring for 30 minutes, the mixture was filtered and the solids were washed thoroughly with THF. The filtrate was concentrated to give 1.60 g (75%) of the desired product as a white foam which was used without further purification: ¹H-NMR (300 MHz, DMSO) δ 7.40 (d, J=8.2 Hz, 2H), 7.33 (d, J=7.6 Hz, 1H), 7.16 (d, J= 8.1 Hz, 2H), 6.90 (d, J=7.7 Hz, 2H), 6.75 (d, J=7.8 Hz, 2H), 6.66 (s, 1H), 6.45 (d, J=7.6 Hz, 1H), 5.69 (s, 1H), 5.64 (s, 1H), 3.95 (t, J=5.5 Hz, 2H), 3.72 (s, 3H), 3.64 (s, 3H), 2.65–2.85 (m, 4H), 2.40–2.65 (m, 6H), 1.60–1.80 (m, 4H); MS (FD) m/e 485 (M+).

EXAMPLE 18

[2-(4-Methoxyphenyl-6-methoxynaphthalen-1-yl][4-[2-(1-pyrrolidinyl)ethoxy] phenyl]methane hydrochloride

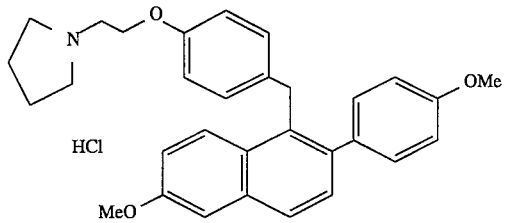

To a solution of the product of Example 17 (1.61 g, 3.30 mmol) stirring in ethyl acetate (50 mL) at ambient temperature was added a saturated solution of hydrochloric acid gas in ethyl acetate (50 mL). The resulting mixture was concentrated to give 1.66 g (100%) of the desired product as a white foam which was used without further purification: ¹H-NMR (300 MHz, DMSO) δ 7.70–7.80 (m, 2H), 7.30–7.40 (m, 2H), 7.20–7.30 (m, 2H), 7.05 (m, 1H), 6.80–7.00 (m, 6H), 4.29 (s, 2H), 4.20–4.25 (m, 2H), 3.84 (s, 3H), 3.75 (s, 3H), 3.42–3.75 (m, 4H), 3.00–3.15 (m, 2H), 1.80–2.00 (m, 4H); MS (FD) m/e 467 (M⁺-hydrochloric acid).

EXAMPLE 19

[2-(4-Hydroxyphenyl-6-hydroxynaphthalen-1-yl][4-[2-(1-pyrrolidinyl)ethoxy] phenyl]methane

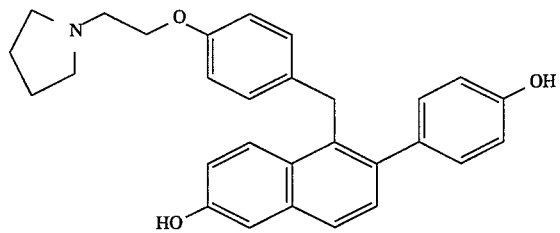

To a solution of the product of Example 18 (1.62 g, 2.60 mmol) in 1.2-dichloroethane (30 mL) stirring at 0° C. was added boron trichloride (10 ml, 117 mmol). The resulting dark purple solution was stirred overnight at ambient temperature in a sealed tube. After cooling the solution to 0° C., methanol )25 mL) was carefully added over a period of 30 minutes (caution, gas evolution). The solution was subsequently concentrated and the resulting material dissolved in 30% isopropanol/chloroform then washed with saturated sodium bicarbonate, brine, dried over anhydrous sodium sulfate, filtered, and concentrated. The crude material was purified by radial chromatography (methanol/chloroform gradient) to give 0.34 g (27%) of the desired product as a white foam: $^1$H-NMR (300 MHz, DMSO-d$_6$) δ 9.45 (s, 1H), 9.36 (s, 1H), 7.72 (d, J=8.8 Hz, 1H), 7.62 (d, J= 9.2 Hz, 1H), 7.28 (d, J=8.7 Hz, 1H), 7.00–7.10 (m, 2H), 6.80–6.90 (m, 2H), 6.70–6.80 (m, 4H), 5.45 (s, 1H), 4.84 (s, 1H), 4.25 (s, 2H), 3.90–4.05 (m, 2H), 2.75–2.90 (m, 2H), 2.50– 2.65 (m, 4H), 1.60–1.80 (m, 4H); $^{13}$C-NMR (75 MHz, DMSO-d$_6$) δ 203.32, 191.97, 188.16, 186.14, 185.95, 177.43, 173.46, 169.60, 167.74, 163.48, 162.30, 159.87, 158.14, 154.98, 152.43, 60.50, 56.25, 54.00, 45.05, 41.00, 37.50, 35.00, 30.05, 27.50, 26.00, 22.50, 20.00; Anal. Calc'd. for: C, 79.24; H, 6.65; N, 3.19. Found: C, 78.99; H, 6.51; N, 2.92; MS (FD) m/e 440 (M+); IR (KBr) 3382.61, 2964.00, 1610.77, 1509.49 cm$^{-1}$.

PREPARATION 8

[3,4-Dihydro-2-(4-methoxyphenyl)-6-methoxynaphthalen-1-yl] [4-[2-(1-N,N-dimethylamino)ethoxy]phenyl]methanone

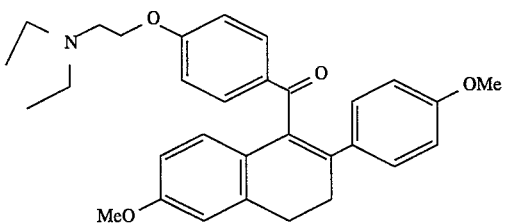

Reaction of the product of Preparation 2 (1.6 g, 4.1 mmol), 2-diethylaminoethylchloride hydrochloride (0.8 g, 4.5 mmol), and potassium carbonate (2.3 g, 16.4 mmol) in dimethylformamide (50 mL) according to the preparation of Preparation 3 gave a 95% yield of the desired product: $^1$H-NMR (300 MHz, CDCl$_3$) δ 7.82 (d, J=8.8 Hz, 2H), 7.20 (d, J=8.7 Hz, 2H), 6.89 (d, J=8.5 Hz, 1H), 6.65–6.80 (m, 5H), 6.62 (m, 1H), 4.03 (t, J=6.3 Hz, 2H), 3.80 (s, 3H), 3.72 (s, 3H), 3.03 (t, J=7.7 Hz, 2H), 2.75– 2.90 (m, 4H), 2.61 (ABq, J=7.2 Hz, ΔV=14.4 Hz, 4H), 1.06 (t, J=7.2 Hz, 6H); MS (FD) m/e 485 (M+); Anal. Calc'd. for: C, 76.67; H, 7.26; N, 2.88. Found: C, 76.97; H, 7.43; N, 2.91.

PREPARATION 9

[3,4-Dihydro-2-(4-methoxyphenyl)-2,4-dihydro-6-methoxynaphthalen-1-yl][4-[3-(1-piperdinyl)propoxy] phenyl]methanone

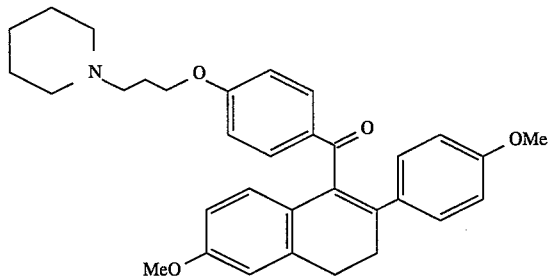

Reaction of the product of Preparation 2 (1.6 g, 4.1 mmol), 1-( 3-chloropropyl)piperidine hydrochloride (0.9 g, 4.5 mmol), and potassium carbonate (2.3 g, 16.4 mmol) in DMF (50 mL) according to the procedure in preparation 7 gave a 95% yield of the desired product: $^1$H-NMR (300 MHz, CDCl$_3$) δ 7.80 (d, J=8.7 Hz, 2H), 7.19 (d, J=5.0 Hz, 2H), 6.86 (d, J=8.4 Hz, 1H), 6.63– 6.80 (m, 5H), 6.60 (m, 1H), 3.98 (t, J=6.4 Hz, 2H), 3.78 (s, 3H), 3.70 (s, 3H), 3.00 (t, J=7.7 Hz, 2H), 2.75–2.85 (m, 2H), 2.30–2.50 (m, 6H), 1.90–2.00 (m, 2H), 1.50–1.65 (m, 4H), 1.40– 1.50 (m, 2H); MS (FD) m/e 511 (M+); Anal. Calc'd. for: C, 77.47; H, 7.29; N, 2.74. Found: 77.42; H, 7.36; N, 2.72.

EXAMPLE 20

[3,4-Dihydro-2-(4-methoxyphenyl)-6-methoxynaphthalen-1-yl] [4-[2-(1-N,N-diethylamino)ethoxy]phenyl]methanol

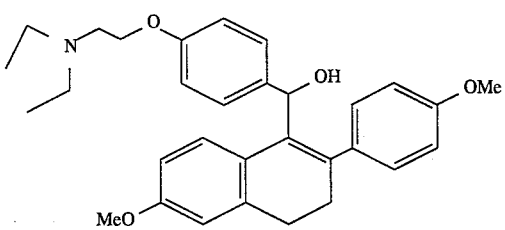

Reaction of the product of Preparation 8 (1.7 g, 3.4 mmol) with lithium aluminum hydride (0.3 g, 6.8 mmol) in THF (80 mL) according to the procedure in Example 17 gave a quantitative yield of the desired product: $^1$H-NMR (300 MHz, CDCl$_3$), δ 7.33 (d, J=8.5 Hz, 2H), 7.20–7.30 (m, 3H), 6.80–6.90 (m, 4H), 6.71 (s, 1H), 6.50 (m, 1H), 5.85 (d, J=3.9 Hz, 1H), 4.01 (t, J=6.4 Hz, 2H), 3.78 (s, 3H), 3.74 (s, 3H), 2.86 (ABq, J=8.2 Hz, Δv= 14.7 Hz, 4H), 2.60–2.70 (m, 6H), 1.85 (m, 1H), 1.05 (t, J=7.2 Hz, 6H); MS (FD) m/e 487 (M+).

EXAMPLE 21

[3,4-Dihydro-2-(4-methoxyphenyl)-6-methoxynaphthalen-1-yl] [4-[3-(1-piperdinyl)propoxy]phenyl]methanol

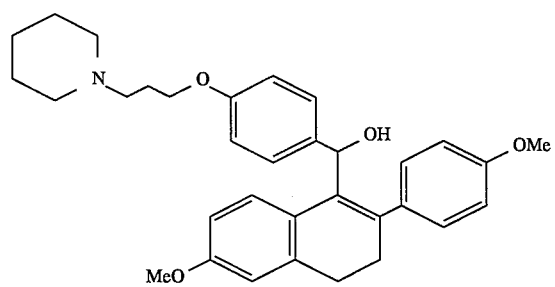

Reaction of the product of Preparation 9 (1.77 g, 3.50 mmol) with lithium aluminum hydride (0.27 g, 7.00 mmol) in THF (50 mL) according to the procedure in Example 17 gave a 97% yield of the desired product: $^1$H-NMR (300 MHz, CDCl$_3$) δ 7.32 (d, J=8.4 Hz, 2H), 7.20–7.30 (m, 4H), 6.80–6.90 (m, 3H), 6.70 (s, 1H), 6.50 (m, 1H), 5.85 (s, 1H), 3.96 (t, J=6.3 Hz, 2H), 3.78 (s, 3H), 3.74 (s, 3H), 2.85–2.95 (m, 2H), 2.60–2.70 (m, 2H), 2.25–2.50 (m, 6H), 1.90–2.00 (m, 2H), 1.54–1.60 (m, 4H), 1.43 (s, 2H); MS (FD) m/e 514 M$^{+1}$).

EXAMPLE 22

[2-(4-Methoxyphenyl)-6-methoxynaphthalen-1-yl][4-[2-(1-N,N-dimethylamino)ethoxy]phenyl]methane hydrochloride

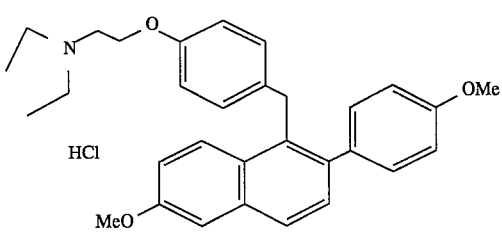

Reaction of the product of Example 20 (1.6 g, 3.3 mmol) with hydrochloric acid (100 mL of a saturated ethyl acetate solution) in ethyl acetate (100 mL) according to the procedure in Example 18 gave a 90% yield of the desired product: IR (KBr) 3416.37, 2935.07, 2835.72, 2575.30, 2437.37, 1624.27, 1608.84, 1510.45 cm$^{-1}$; $^1$H-NMR (300 MHz, CDCl$_3$) δ 7.72 (t, J=8.6 Hz, 2H), 7.15– 7.30 (m, 4H), 7.05 (m, 1H), 6.85–6.95 (m, 3H), 6.72 (d, J=8.6 Hz, 2H), 4.40–4.50 (m, 2H), 4.35 (s, 3H), 3.92 (s, 3H), 3.83 (s, 3H), 3.35–3.45 (m, 2H), 3.20–3.35 (m, 4H), 1.43 (t, J=7.2 Hz, 6H); MS (FD) m/e 470 (M+-hydrochloric acid); Anal. Calc'd. for: C, 73.57; H, 7.17; N, 2.77. Found: C, 73.80; H, 7.35; N, 2.77.

EXAMPLE 23

[2-(4-(Methoxyphenyl)-6-methoxynaphthalen-1-yl][4-[3-(1-piperdinyl)propoxy] phenyl]methane hydrochloride

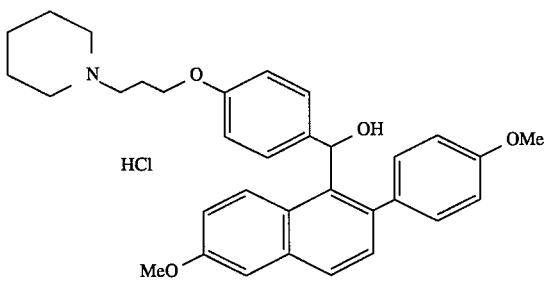

Reaction of the product of Example 21 (1.5 g, 2.9 mmol) with hydrochloric acid (50 mL of a saturated ethyl acetate solution) in ethyl acetate (50 mL) according to the procedure in Example 18 gave a 97% yield of the desired product: $^1$H-NMR (300 MHz, CDCl$_3$) δ 7.70–7.80 (m, 2H), 7.42 (d, J=8.4 Hz, 1H), 7.15–7.30 (m, 3H), 7.05 (m, 1H), 6.85–6.95 (m, 4H), 6.69 (d, J=8.6 Hz, 2H), 4.34 (s, 2H), 3.97–4.03 (m, 2H), 3.92 (s, 3H), 3.82 (s, 3H), 3.50–3.60 (m, 2H), 3.05–3.20 (m, 2H), 2.57–2.70 (m, 2H), 2.20–2.50 (m, 4H), 1.80–2.00 (m, 4H); MS (FD) m/e 495 (M$^+$ -hydrochloric acid); Anal. Calc'd. for: C, 74.49; H, 7.20; N, 2.63. Found: C, 74.74; H, 7.36; N, 2.75.

EXAMPLE 24

[2-(4-hydroxyphenyl)-6-hydroxynaphthalen-1-yl][4-[2-(1-N,N-diethylamino)ethoxy]phenyl]methane

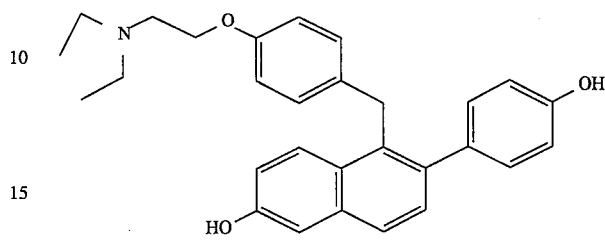

Reaction of the product of Example 22 (1.32 g, 2.60 mmol) with boron trichloride (10.0 mL, 117.0 mmol) in 1,2-dichloroethane (30 mL) according to the procedure in Example 19 gave a 76% yield of the desired product as a white powder: IR (KBr) 3356.57, 2973.65, 1734.23, 1704.33, 1610.77, 1509.49 cm$^{-1}$; $^1$H-NMR (300 MHz, DMSO-d$_6$) δ 9.62 (s, 1H), 9.43 (s, 1H), 7.56–7.70 (m, 2H), 7.24 (d, J=8.4 Hz, 1H), 7.00–7.15 (m, 3H), 6.95 (m, 1H), 6.82 (d, J=8.6 Hz, 2H), 6.65–6.78 (m, 4H), 4.23 (s, 2H), 4.00 (t, J=6.4 Hz, 2H), 2.65–2.75 (m, 2H), 2.40–2.60 (m, 4H), 0.90 (t, J=7.1 Hz, 6H); $^{13}$C-NMR (75 MHz, DMSO-d$_6$) δ 156.53, 156.45, 154.87, 136.65, 134.44, 133.49, 132.66, 132.28, 130.14, 128.90, 128.73, 126.93, 126.57, 125.18, 118.73, 115.01, 114.32, 109.43, 66.22, 51.43, 47.00, 39.00, 33.81, 11.87; MS (FD) m/e 442 (M+); HRMS (FAB+) for C$_{29}$H$_{31}$NO$_3$ calculated 442.2382, found 442.2381.

PREPARATION 10

[3,4-Dihydro-2-(4-methoxyphenyl)-6-methoxynaphthalen-1-yl] [4-[2-(1-bromo)ethoxy]phenyl]methanone

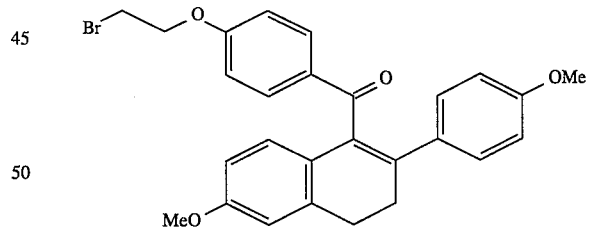

To a solution of the product of Preparation 2 (4.00 g, 10.0 mmol) stirring in 2-butanone (100 mL) at ambient temperature was added potassium carbonate (2.76 g, 20.0 mmol) and 1,2-dibromoethane (17.2 ml, 100 mmol). This solution was refluxed overnight then filtered and concentrated. The resulting brown oil was purified by flash chromatography (silica gel, 20% ethyl acetate/hexanes) to give 4.40 g (89%) of the desired product as a brown oil. $^1$H-NMR (300 MHz, CDCl$_3$) δ 7.81 (d, J=8.7 Hz, 2H), 7.18 (d, J=8.7 Hz, 2H), 6.86 (d, J=8.6 Hz, 1H), 6.76 (d, J= 8.7 Hz, 3H), 6.78 (d, J=6.8 Hz, 2H), 6.60 (m, 1H), 4.26 (t, J= 6.1 Hz, 2H), 3.78 (s, 3H), 3.70 (s, 3H), 3.60 (t, J=6.4 Hz, 2H), 3.01 (t, J=7.7 Hz, 2H), 2.75–2.85 (m, 2H); Anal. Calc'd. for: C, 65.73; H, 5.11. Found: C, 65.96; H, 5.28.

PREPARATION 11

[3,4-Dihydro-2-(4-methoxyphenyl)-6-methoxynaphthalen-1-yl] [4-[2-(1-hexamethyleneiminyl)ethoxy]phenyl]methanone

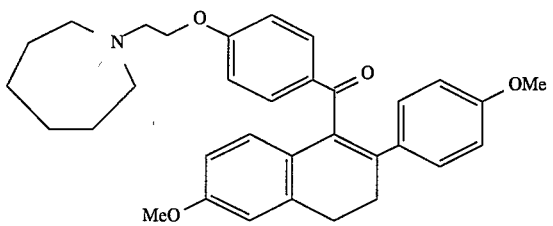

To a solution of the product of Preparation 10 (2.1 g, 4.3 mmol) stirring in dimethylformamide (50 mL) at ambient temperature was added potassium carbonate (1.8 g, 13 mmol) and hexamethyleneimine (0.9 ml, 13 mmol). The solution was subsequently heated to 100° C. After stirring overnight, the mixture was concentrated and the resulting brown oil partitioned between chloroform and water. The organic extract was washed with brine, dried, (sodium sulfate), filtered, and concentrated. The resulting yellow oil was purified by radial chromatography (ethyl acetate/hexanes/methanol gradient) to give 0.95 g (43%) of the desired product as a yellow oil: $^1$H-NMR (300 MHz, CDCl$_3$) δ 7.81 (d, J=8.7 Hz, 2H), 7.21 (d, J=6.9 Hz, 1H), 6.81 (d, J=8.5 Hz, 1H), 6.60–6.85 (m, 7H), 4.00–4.50 (m, 2H), 3.80 (s, 3H), 3.72 (s, 3H), 2.85–3.10 (m, 4H), 2.70–2.85 (m, 6H), 1.50–1.80 (m, 8H); Anal. Calc'd. for: C, 77.47; H, 7.29; N, 2.74. Found: C, 77.25; H, 7.16; N, 2.71; MS (FD) m/e 511 (M+).

EXAMPLE 25

[3,4-Dihydro-2-(4-methoxyphenyl)-6-methoxynaphthalen-1-yl] [4-[2-(1-hexamethyleneimine)ethoxy]phenyl]methanol

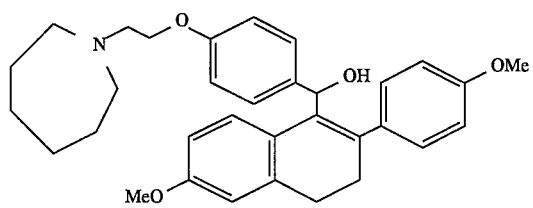

To a suspension of lithium aluminum hydride (0.3 g, 7.2 mmol) stirring at 0° C. in THF (40 mL) was slowly added a solution of the product of Preparation 11 (1.8 g, 3.6 mmol) in THF (25 mL) over a 5 minutes period. The reaction mixture was allowed to warmed to ambient temperature. After 1 hours, the mixture was cooled to 0° C. and quenched carefully with water (0.4 mL). To this solution, sodium hydroxide (1.2 mL of 15% w/w aqueous solution) was slowly added followed by water (0.4 mL). After stirring for 30 minutes, the mixture was filtered and the solids were washed thoroughly with THF. The filtrate was concentrated to give 1.71 g (93%) of the desired product as a white foam which was used without further purification: $^1$H-NMR (300 MHz, CDCl$_3$) δ 7.34 (d, J=8.5 Hz, 2H), 7.20–7.30 (m, 3H), 6.80–6.90 (m, 4H), 6.73 (s, 1H), 6.55 (m, 1H), 5.88 (s, 1H), 4.06 (t, J= 6.3 Hz, 2H), 3.81 (s, 3H), 3.76 (s, 3H), 2.85–3.00 (m, 4H), 2.75–2.85 (m, 4H), 2.63–2.75 (m, 2H), 2.95 (m, 1H), 1.60–1.75 (m, 8H), Anal. Calc'd. for: C, 77.16; H, 7.65; N, 2.73. Found: C, 77.33; H, 7.79; N, 2.71; MS (FD) m/e 513 (M+).

EXAMPLE 26

[2-(4-Methoxyphenyl)-6-methoxynaphthalen-1-yl][4-[2-(1-hexamethyleneiminyl)ethoxy]phenyl]methane hydrochloride salt

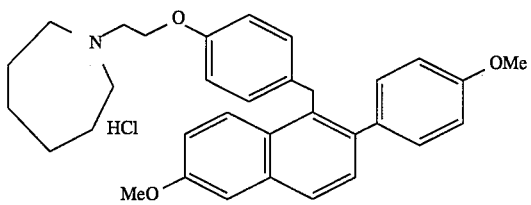

To a solution of the product of Example 25 (1.7 g, 3.3 mmol) stirring in ethyl acetate (100 mL) at ambient temperature was added hydrochloric acid (100 mL of a saturated solution in ethyl acetate). The resulting mixture was concentrated to give 1.66 g (94%) of the desired product which was used without purification: $^1$H-NMR (300 MHz, CDCl$_3$) δ 7.48 (t, J=8.9 Hz, 2H), 7.43 (d, J=8.6 Hz, 1H), 7.20–7.35 (m, 3H), 7.10 (m, 1H), 6.85–7.00 (m 4H), 6.75 (d, J=8.6 Hz, 2H), 4.45–4.60 (m, 2H), 4.37 (s, 2H), 3.94 (s, 3H), 3.85 (s, 3H), 3.55–3.70 (m, 2H), 3.40–3.50 (m, 2H), 3.00–3.20 (m, 2H), 2.10–2.25 (m, 2H), 1.80– 2.00 (m, 4H), 1.60–1.80 (m, 2H); $^{13}$C-NMR (75 MHz, DMSO) δ 155.6, 137.15, 134.29, 134.19, 134.08, 132.29, 130.15, 129.01. 128.79, 127.28, 126.91, 125.95, 124.94, 118.63, 114.61, 113.70, 106.79, 64.42, 55.20, 55.13, 55.10, 54.85, 54.10, 33.77, 30.44, 26.05, 22.72; Anal. Calc'd. for: C, 74.49; H, 7.20; N, 2.63. Found: C, 74.73; H, 7.16; N, 2.62; MS (FD) m/e 495 (M+-hydrochloric acid): IR (KBr) 2934.10, 2862.73, 2835.72, 2448.94, 1624.27, 1608.84, 1511.42 cm$^{-1}$.

EXAMPLE 27

[2-(4-Hydroxyphenyl)-6-hydroxynaphthalen-1-yl][4-[2-(1-hexamethyleneiminyl)ethoxy]phenyl]methane

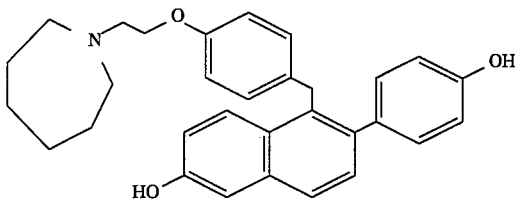

To a solution of the product of Example 26 (1.3 g, 2.4 mmol) stirring in 1,2-dichloroethane (30 mL) at 0° C. was added boron trichloride (10 mL, 117 mmol). The resulting dark purple solution was stirred overnight at ambient temperature in a sealed tube then cooled to 0° C. Methanol (25 mL) was slowly added over a period of 30 minutes (caution: gas evolution) and the resulting solution was concentrated. The crude material was dissolved in 20% methanol/chloroform and subsequently washed with saturated sodium bicarbonate and brine. The organic extract was dried (sodium sulfate), filtered, and concentrated. The resulting brown foam was purified by radial chromatography (ethyl acetate/triethylamine/methanol/hexanes gradient) to provide a tan solid.

This material was dissolved in ethyl acetate then washed with saturated sodium bicarbonate. The organic extract was concentrated to give 0.60 g (54%) of the desired product as a white foam: $^1$H-NMR (300 MHz, DMSO-d$_6$) δ 9.64 (s, 1H), 9.41 (s, 1H), 7.55–7.70 (m, 2H), 7.24 (d, J=8.5 Hz, 1H), 7.00–7.10 (m, 3H), 6.95 (m, 1H), 6.81 (d, J=8.6 Hz, 2H), 6.70–6.78 (m, 4H), 4.23 (s, 2H), 3.91 (t, J=6.0 Hz, 2H), 2.70–2.80 (m, 2H), 2.55–2.70 (m, 4H), 1.40–1.60 (m, 8H); Anal. Calc'd. for: C, 79.63; H, 7.11; N, 2.99. Found: C, 79.35; H, 6.87; N, 2.75; MS (FD) m/e 468 (M+); IR (KBr) 3362.35, 2926.39, 2855.98, 1734.23, 1704.33, 1610.77, 1509.49 cm$^{-1}$.

PREPARATION 12

[3,4-Dihydro-2-(4-methoxyphenyl)-3,4-dihydro-6-methoxynaphthalen-1-yl][4-[2-(1-morpholinyl)ethoxy]phenyl]methanone

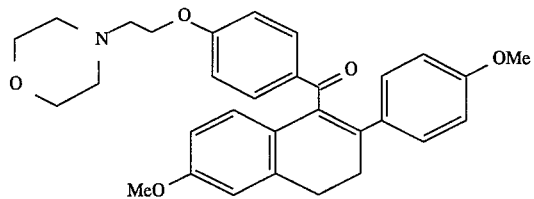

Reaction of the product of Preparation 10 (2.1 g, 4.3 mmol), morpholine (1.13 mL, 12.9 mmol), and potassium carbonate (1.78 g, 12.9 mmol) in DMF (50 mL) according to the procedure in Preparation 11 gave a 80% yield of the desired product as a thick oil: $^1$H-NMR (300 MHz, CDCl$_3$) δ 7.83 (d, J=8.7 Hz, 2H), 7.60 (m, 1H), 7.20 (d, J=8.8 Hz, 2H), 6.88 (d, J=8.7 Hz, 1H), 6.65–6.80 (m, 5H), 4.05–4.20 (m, 2H), 3.80 (s, 3H), 3.73 (s, 3H), 3.70–3.80 (m, 4H), 2.90 (t, J=7.9 Hz, 2H), 2.75–2.85 (m, 4H), 2.50–2.60 (m, 4H); MS (FD) m/e 499 (M+); Anal. Calc'd. for: C, 74.53; H, 6.66; N, 2.80. Found: C, 74.75; H, 6.58; N, 2.83.

PREPARATION 13

[3,4-Dihydro-2-(4-methoxyphenyl)-6-methoxynaphthalen-1-yl][4-[2-(1-(3,3-dimethyl(pyrrolidinyl)ethoxy]phenyl]methanone

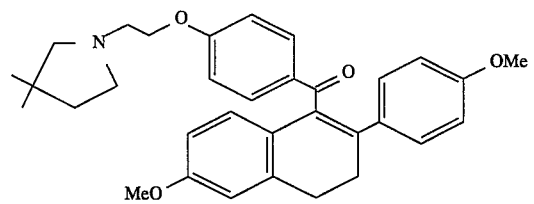

Reaction of the product of Preparation 10 (2.1 g, 4.3 mmol), 3,3-dimethylpyrrolidine (1.2 g, 12 mmol), and potassium carbonate (1.8 g, 13 mmol) in DMF (100 mL) according to the procedure in Preparation 11 gave a 60% yield of the desired product as a thick oil: $^1$H-NMR (300 MHz, CDCl$_3$) δ 7.80 (d, J=8.7 Hz, 2H), 7.18 (d, J=8.7 Hz, 2H), 6.87 (d, J=8.6 Hz, 1H), 6.73–6.80 (m, 3H), 6.67 (d, J→8.6 Hz, 2H), 6.60 (m, 1H), 4.05 (m, 2H), 3.78 (s, 3H), 3.71 (s, 3H), 2.89–3.05 (m, 2H), 2.73–2.86 (m, 4H), 2.64–2.75 (m, 2H), 2.04 (s, 2H), 1.60 (t, J=6.9 Hz, 2H), 1.07 (s, 6H); MS (FD) m/e 511 (M+).

EXAMPLE 28

[3,4-Dihydro-2-(4-methoxyphenyl)-6-methoxynaphthalen-1-yl][4-[2-(1-morpholinyl)ethoxy]phenyl]methanol

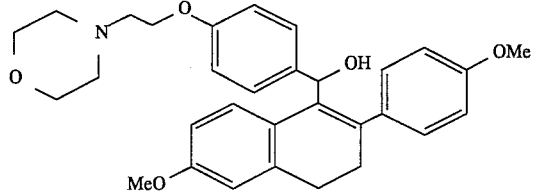

Reaction of the product of Preparation 12 (1.6 g, 3.2 mmol) with lithium aluminum hydride (0.3 g, 7.2 mmol) in THF (65 mL) according to the procedure in Example 25 gave a 98% yield of the desired product as a white foam: $^1$H-NMR (300 Hz, CDCl$_3$) δ 7.39 (d, 8.7 Hz, 2H), 7.20–7.30 (m, 4H), 6.80–7.00 (m, 3H), 6.73 (m, 1H), 6.55 (m, 1H), 5.86 (d, J=4.2 Hz, 1H), 4.09 (t, J=5.6 Hz, 2H), 3.80 (s, 3H), 3.70–3.80 (m, 4H), 3.76 (s, 3H), 2.85–3.00 (m, 2H), 2.75–2.85 (m, 2H), 2.65 (m, 1H), 2.55–2.65 (m, 4H), 1.05–1.10 (m, 2H); MS (FD) m/e 501 (M+); Anal. Calc'd. for: C, 74.23; H, 7.03; N, 2.79. Found: C, 74.51; H, 7.18; N, 2.79.

EXAMPLE 29

[3,4-Dihydro-2-(4-methoxyphenyl)-6-methoxynaphthalen-1-yl[[4-[2-(1-(3,3-dimethyl)pyrrolidinyl)ethoxy]phenyl]methanol

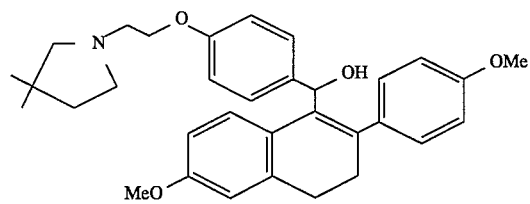

Reaction of the product of Preparation 13 (1.3 g, 2.5 mmol) with lithium aluminum hydride (0.2 g, 5.0 mmol) in THF (65 mL) according to the procedure in Example 25 gave a 98% yield of the desired product as a white foam: $^1$H-NMR (300 MHz, CDCl$_3$) δ 3.33 (d, J=8.6 Hz, 2H), 7.20–7.30 (m, 3H), 6.80–6.90 (m, 4H), 6.70 (m, 1H), 6.52 (m, 1H), 5.85 (s, 1H), 4.04 (t, J=6.1 Hz, 2H), 3.79 (s, 3H), 3.74 (s, 3H), 2.80–2.95 (m, 4H), 2.60–2.75 (m, 4H), 2.42 (s, 2H), 2.20 (m, 1H), 1.85 (m, 1H), 1.61 (m, 1H), 1.08 (s, 6H); MS (FD) 513 (M+); Anal. Calc'd. for: C, 77.16, H, 7.65, N, 2.73. Found: C, 77.33; H, 7.51; N, 2.69.

EXAMPLE 30

[2-(4-Methoxyphenyl)-6-methoxynaphthalen-1-yl][4-[2-(1-morpholinyl)ethoxy]phenyl]methane hydrochloride

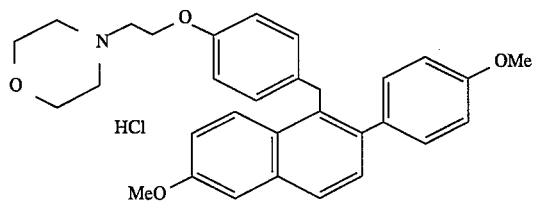

Reaction of the product of Example 28 (1.58 g, 3.1 mmol) with hydrochloric acid (100 mL of a saturated solution in ethyl acetate) in ethyl acetate (100 mL) according to the procedure in Example 26 gave a 94% yield of the desired product as a white foam: $^1$H-NMR (300 MHz, CDCl$_3$) δ 7.70–7.85 (m, 2H), 7.44 d, J= 8.4 Hz, 1H), 7.20–7.40 (m, 4H), 6.86–7.15 (m, 4H), 6.70–6.86 (m, 2H), 4.50–4.65 (m, 2H), 4.25–4.50 (m, 4H), 3.83–4.10 (m, 2H), 3.94 (s, 3H), 3.85 (s, 3H), 3.50–3.70 (m, 2H), 3.40–3.50 (m, 2H), 3.00–3.20 (m, 2H), MS (FD) m/e 483 (M+-hydrochloric acid).

EXAMPLE 31

[2-(4-Methoxyphenyl)-6-methoxynaphthalen-1-yl][4-[2-(1-(3,3-dimethyl)pyrrolidinyl)ethoxy]phenyl]methane hydrochloride

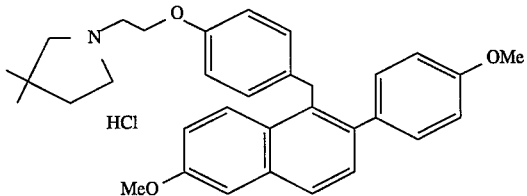

Reaction of the product of Example 29 (1.2 g, 2.4 mmol) with hydrochloric acid (100 mL of a saturated solution in ethyl acetate) in ethyl acetate (100 mL) according to the procedure in Example 26 gave a 92% yield of the desired product as a white foam: $^1$H-NMR (300 MHz, CDCl$_3$) δ 7.29 (t, J=9.3 Hz, 2H), 7.41 (d, J=8.2 Hz, 1H), 7.15–7.30 (m, 3H), 7.19 (d, J=6.8 Hz, 1H), 6.85–7.00 (m, 4H), 6.73 (d, J=7.52 Hz, 2H), 4.48 (s, 2H), 4.35 (s, 2H), 3.93 (s, 3H), 3.83 (s, 3H), 3.60 (m, 1H), 3.15–3.50 (m, 2H), 3.15 (m, 1H), 2.76 (m, 1H), 2.05 (m, 1H), 1.85 (m, 1H), 1.75 (m, 1H), 1.33 (s, 3H), 1.22 (s, 3H); MS (FD) m/e 495 (M+-hydrochloric acid); Anal. Calc'd. for: C, 74.49; H, 7.20; N, 2.63. Found: C, 74.70; H, 7.18; N, 2.47.

EXAMPLE 32

2-(4-Hydroxyphenyl)-6-hydroxynaphthalen-1-yl][4-[2-(1-morpholinyl)ethoxy] phenyl]methane

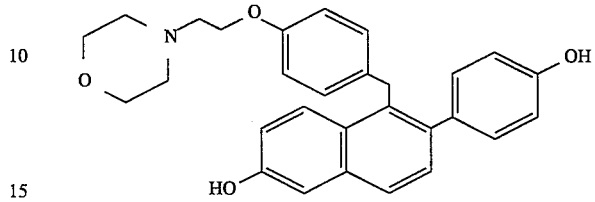

Reaction of the product of Example 30 (1.28 g, 2.40 mmol) with boron trichloride (10 mL, 117 mmol) in 1,2-dichloroethane (30 mL) according to the procedure in Example 27 gave a 28% yield of the desired product as a white solid: IR (KBr) 3317.99, 2927.35, 2868.51, 1610.77, 1509.49 cm$^{-1}$; $^1$H-NMR (300 MHz, CDCl$_3$) δ 7.75 (d, J=9.3 Hz, 1H), 7.55 (m, 1H), 7.37 (d, J=8.5 Hz, 1H), 7.10–7.20 (m, 2H), 6.65–7.05 (m, 8H), 5.50 (br s, 2H), 4.32 (s, 2H), 4.00–4.20 (m, 2H), 3.70–3.80 (m, 4H), 2.70–2.85 (m, 2H), 2.50–2.70 (m, 4H); MS (FD) m/e 456 (M+); Anal. Calc'd. for: C, 76.46; H, 6.42; N, 3.07. Found: C, 76.75; H, 6.44; N, 3.02.

EXAMPLE 33

[2-(4-Hydroxyphenyl)-6-hydroxynaphthalen-1-yl][4-[2-(1-(3,3-dimethyl)pyrrolidinyl)ethoxy]phenyl]methane

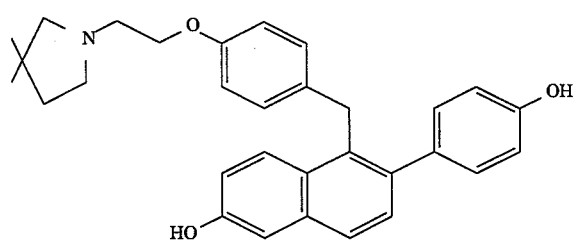

Reaction of the product of Example 31 (1.2 g, 2.3 mmol) with boron trichloride (10 mL, 117 mmol) in 1,2-dichloroethane (30 mL) according to the procedure in Example 27 gave a 58% yield of the desired product as a white solid: IR (KBr) 3370.07, 2955.32, 2869.48, 1711.08, 1610.77, 1510.46 cm$^{-1}$; $^1$H-NMR (300 MHz, CDCl$_3$) δ7.71 (d, J=9.2 Hz, 1H), 6.56 (d, J=8.5 Hz, 1H), 7.32 (d, J=8.4 Hz, 1H), 7.10–7.14 (m, 3H), 6.98 (m, 1H), 6.75– 6.85 (m, 4H), 6.58 (d, J=8.5 Hz, 2H), 4.28 (s, 2H), 4.11 (t, J= 7.70 Hz, 2H), 2.90 (t, J=5.9 Hz, 2H), 2.82 (t, J=6.7 Hz, 2H), 2.79 (t, J=6.7 Hz, 2H), 1.66 (t, J=6.9 Hz, 2H), 1.10 (s, 6H); MS (FD) m/e 468 (M+); Anal. Calc'd. for: C, 79.63; H, 7.11; N, 3.00. Found: C, 79.65; Y, 7.24; N, 2.72.

PREPARATION 14

2-(4-Methoxyphenyl)-6-methoxynaphthalen-1-yl)(4-methoxyphenyl)methanone

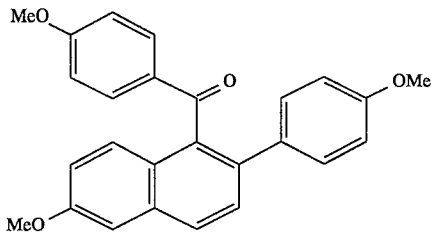

To 50 mL of dioxane were added 6.0 g (15 mmol) of [3,4-Dihydro- 2-(4-methoxyphenyl)-6-methoxynaphthalen-1yl](4-methoxyphenyl)methanone and 7.3 g (32 mmol) of 2,3-dichloro-5,6-dicyano- 1,4-benzoquinone. The mixture was heated to reflux for 2 hours, then allowed to stir at ambient temperature for 60 hours. The mixture was then concentrated to dryness and the residue was taken up in 500 mL of methylene chloride and washed 3 times with 400 mL of 2N sodium hydroxide followed by one washing with 500 mL of deionized water. The resulting organic layer was separated, dried on sodium sulfate, and the solvent was removed under vacuum. The resulting material was then purified by flash chromatography (silica gel, 20% ethyl acetate/hexanes gradient to yield 4.75 g (80%) of the title compound as a white foam: NMR QE300 MHz in $CDCl_3$: (3.80 ppm, s, 3H), (4.00 ppm, s, 3H), (6.75 ppm, d, 2H), (6.85 ppm, d, 2H), (7.20 ppm, dd, 1H) (7.30 ppm, ds, 1H), (7.40 ppm, d, 2H), (7.60 ppm, d, 1H), (7.75 ppm, d, 2H), (7.95 ppm, d, 1H). MS (FD) me/e 398 (M+); Anal. Calc'd. for: C, 78.37; H, 5.57. Found: C, 78.55; H, 5.78.

EXAMPLE 34

[2-(4-Methoxyphenyl)-6-methoxynaphthalen-1-yl][4-[2-(1-piperdinyl)ethoxy] phenyl]methane hydrochloride

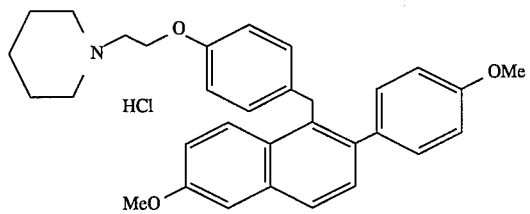

To 20 mL of propyl benzene were added 240 mg (6.01 mmol) of 95% lithium aluminum hydride and 240 mg (0.484 mmol) of the compound from Preparation 14. The mixture was heated to reflux for 35 minutes and allowed to cool to ambient temperature. To the mixture was carefully added 1 mL of deionized water followed by 3 mL of 15% sodium hydroxide/deionized water (w/w), and then another 1 mL of deionized water. The mixture was stirred for 15 minutes at ambient temperature and the precipitate was removed by vacuum filter. The mother liquor was then diluted with methylene chloride (100 mL), washed once with brine, dried on sodium sulfate, and rotovaped to dryness. The brown gum was purified by radial chromatography on a 4 mm plate and 19:1 methylene chloride:methanol as eluent to provide the title compound. NMR QE300 MHz in $CDCl_3$: (1.55 ppm, m, 2H), (1.75 ppm, complex, 4H), (2.60 ppm, complex, 4H), (2.85 ppm, t, 2H), (3.95 ppm, s, 3H), (4.05 ppm, s, 3H), 4.20 ppm, t, 2H:), (4.45 ppm, s, 2H), (6.85 ppm, d, 2H), (7.00 ppm, complex, 4H), (7.15 ppm, dd, 1H), (7.25 ppm, ds, 1H), (7.35 ppm, d, 2H), (7.50 ppm, d, 1H), 7.80 ppm, d, 1H), (7.90 ppm, d, 1H). MS (FD) me/e 481 (M+).

EXAMPLE 35

[2-(4-Hydroxyphenyl)-6-hydroxynaphthalen-1-yl][4-[2-(1-piperdinyl)ethoxy] phenyl]methane

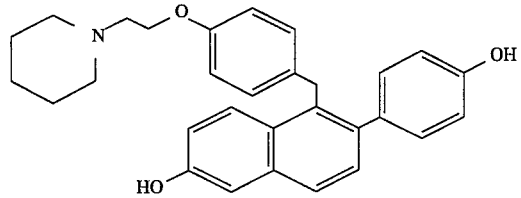

To a suspension of the deprotected product of Preparation 12, such deprotection accomplished via standard procedures as herein described, (0.51 g, 1.00 mmol) stirring in n-propylbenzene is added Red-Al® (0.87 g, 6.00 mmol), and the mixture is heated to reflux. After 3 hours, the solution is cooled to ambient temperature and carefully quenched with excess 1.0N hydrochloric acid. The resulting biphasic mixture is extracted with ethyl acetate and the combined organic extracts washed with saturated aqueous bicarbonate, brine, dried ($MgSO_4$), filtered, and concentrated. Purification of the crude material by radial chromatography (silica gel, ethyl acetate/hexanes/methanol/triethylamine (2.5/2.5/0.7/0.3) provides the title material.

TEST PROCEDURE

General Preparation Procedure

In the examples illustrating the methods, a post-menopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection.

After a one week acclimation period (therefore, two weeks post-OVX) daily dosing with test compound was initiated. 17α-ethynyl estradiol or the test compound were given orally, unless otherwise stated, s a suspension in 1% carboxymethylcellulose or dissolved in 20% cyclodextrin. Animals were does daily for 4 days. Following the dosing regimen, animals were weighed and anesthetized with a ketamine: Xylazine (2.1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis.

Blood samples were allowed to clot at room temperature for 2 hours, and serum was obtained following centrifugation for 10 minutes at 3000 rpm. Serum cholesterol was determined using a Bohringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

Uterine Eosinophil Peroxidase (EPO) Assay.

Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 n. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol ($EE_2$; an orally available form of estrogen), and rats treated with certain compounds of the present invention. Although $EE_2$ caused decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the present invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the below data, estrogenicity also was assessed by evaluating the adverse response of eosinophil infiltration into the uterus. The compounds of the present invention did not cause any increase in the number of eosinophils observed in the stromal layer of ovariectomized rats, while estradiol cause a substantial, expected increase in eosinophil infiltration.

The data presented in the Tables 1 below reflects the response of 5 to 6 rats per treatment.

TABLE 1

| Compound | Dose mg/kg | Uterine Weight (% increase vs. OVX) | Uterine EPO (V. max) | Serum Cholesterol (% decrease vs. OVX) |
|---|---|---|---|---|
| $EE_2$ | 0.1 | 86.3 | 116.4 | 81.4 |
| Example 1 | 0.01 | −11.2 | 4.2 | 42.9 |
|  | 0.1 | 23.1 | 7.2 | 59.9 |
|  | 1.0 | 29.7 | 4.5 | 75.0 |
|  | 10.0 | 12.2 | 3.6 | 63.4 |
| Example 2 | 0.01 | 2.4 | 4.5 | 34.2 |
|  | 0.1 | 24.6 | 4.5 | 63.0 |
|  | 1.0 | 4.1 | 4.8 | 78.1 |
|  | 10.0 | 2.6 | 4.2 | 58.8 |
| Example 3 | 0.01 | 2.0 | 5.4 | 33.3 |
|  | 0.1 | 7.1 | 4.2 | 56.7 |
|  | 1.0 | 0.0 | 4.2 | 63.6 |
|  | 10.0 | 4.5 | 4.8 | 74.7 |
| Example 4 | 0.01 | — | — | — |
|  | 0.1 | 52.1 | 3.6 | 21.2 |
|  | 1.0 | 22.8 | 2.9 | 37.2 |
|  | 10.0 | 75.2 | 3.4 | 20.8 |
| Example 5 | 0.01 | — | — | — |
|  | 0.1 | 43.2 | 3.4 | 6.0 |
|  | 1.0 | 16.0 | 4.3 | 62.0 |
|  | 10.0 | 25.3 | 2.6 | 46.2 |
| Example 11 | 0.01 | — | — | — |
|  | 0.1 | 48.1 | 4.8 | 60.2 |
|  | 1.0 | 47.4 | 3.9 | 73.5 |
|  | 10.0 | 14.4 | 3.9 | 72.4 |
| Example 12 | 0.01 | — | — | — |
|  | 0.1 | 26.3 | 12.0 | 46.3 |
|  | 1.0 | 18.6 | 4.8 | 49.9 |
|  | 10.0 | 25.1 | 4.5 | 50.1 |
| Example 15 | 0.01 | 29.3 | 4.6 | 12.4 |
|  | 0.1 | 41.6 | 7.0 | 53.4 |
|  | 1.0 | 21.2 | 5.2 | 66.0 |
|  | 10.0 | 53.7 | 5.5 | 55.4 |
| Example 19 | 0.01 | — | — | — |
|  | 0.1 | −12.4 | 0.9 | 4.5 |
|  | 1.0 | 1.0 | 5.4 | 19.7 |
|  | 10.0 | 7.1 | 4.5 | 40.9 |
| Example 22 | 0.01 | — | — | — |
|  | 0.1 | 83.9 | 45.0 | 72.0 |
|  | 1.0 | 87.5 | 41.1 | 60.5 |
|  | 10.0 | 89.3 | 46.2 | 68.7 |
| Example 24 | 0.01 | — | — | — |
|  | 0.1 | 87.7 | 13.8 | 69.2 |
|  | 1.0 | 77.8 | 55.8 | 50.0 |
|  | 10.0 | 86.7 | 36.3 | 48.4 |
| Example 26 | 0.01 | — | — | — |
|  | 0.1 | 32.4 | 5.4 | 45.1 |
|  | 1.0 | 64.2 | 9.9 | 55.5 |
|  | 10.0 | 48.0 | 9.9 | 60.6 |
|  | 0.1 | 48.4 | 12.0 | 56.9 |
|  | 1.0 | 23.2 | 7.2 | 68.1 |
|  | 10.0 | 38.8 | 4.2 | 56.6 |
| Example 32 | 0.01 | — | — | — |
|  | 0.1 | 50.5 | 9.3 | 57.9 |
|  | 1.0 | 55.4 | 39.3 | 60.3 |
|  | 10.0 | 69.7 | 34.8 | 65.7 |
| Example 33 | 0.01 | — | — | — |
|  | 0.1 | 40.8 | 12.9 | 25.2 |
|  | 1.0 | 79.0 | 55.2 | 41.1 |
|  | 10.0 | 63.0 | 73.5 | 52.8 |

In addition to the demonstrated benefits of the compounds of the present invention, especially when compared to estradiol, the above data clearly demonstrate that compounds of Formula I are not estrogen mimetics. Furthermore, no deleterious toxicological effects (survival) were observed with any treatment.

Osteoporosis Test Procedure

Following the General Preparation Procedure, infra, the rats were treated daily for 35 day (6 rats per treatment group) and sacrificed by carbon dioxide asphyxiation on the 36th day. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

The right femurs were excised and digitilized x-rays generated and analyzed by an image analysis program (NIH image) at the distal metaphysis. The proximal aspect of the tibiae from these animals were also scanned by quantitative computed tomography.

In accordance with the above procedures, compounds of the present invention and ethynyl estradiol ($EE_2$) in 20% hydroxypropyl β-cyclodextrin were orally administered to test animals. Distal femur metaphysis data presented in Tables 2 and 3 below are the results of formula I compound treatments compared to intact and ovariectomized test animals. Results are reported as the mean ±the standard error of the mean.

TABLE 2

| Compound/Treatment | Dose/kg | Distal Femur Metaphysis (X-ray Image Analysis-Gray Score) |
| --- | --- | --- |
| Sham (20% cyclodextrin) | — | 30.5 ± 4.3* |
| Overiectomy control (20% cyclodextrin) | — | 5.5 ± 0.6 |
| EE2 | 0.1 mg | 32.8 ± 7.9* |
| Example 1 | 0.1 mg | 24.7 ± 4.2* |
|  | 1.0 mg | 21.7 ± 4.7* |
|  | 10.0 mg | 21.9 ± 3.2 |
| Example 3 | 0.1 mg | 14.5 ± 3.6 |
|  | 1.0 mg | 31.4 ± 5.8* |
|  | 10.0 mg | 26.6 ± 6.3* |

*P <= 0.5 two tailed Student's T Test on raw data.

TABLE 3

| Compound/Treatment | Dose/kg | Distal Femur Metaphysis (X-ray Image Analysis-Gray Score) |
| --- | --- | --- |
| Sham (20% cyclodextrin) | — | 44.7 ± 6.4* |
| Overiectomy control (20% cyclodextrin) | — | 7.2 ± 2.2 |
| EE2 | 0.1 mg | 44.4 ± 4.8 |
| Example 2 | 0.01 mg | 19.6 ± 3.3 |
|  | 0.1 mg | 25.7 ± 5.9* |
|  | 1.0 mg | 21.5 ± 3.2* |
|  | 10.0 mg | 30.0 ± 4.5 |

*P <= 0.05 two tailed Student's T Test on raw data.?

In summary, ovariectomy of the test animals caused a significant reduction in femur density compared to intact, vehicle treated controls. Orally administered ethynyl estradiol ($EE_2$) prevented this loss, but the risk of uterine stimulation with this treatment is ever-present.

The compounds of the present invention also prevented bone loss in a general, dose-dependent manner. Accordingly, the compounds of the present invention are useful for the treatment of post-menopausal syndrome, particularly osteoporosis.

MCF-7 Proliferation Assay

MCF-7 breast adenocarcinoma cells (ATCC HTB 22) were maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium (Ca++/Mg++ free HBSS (phenol red-free) supplemented with 10 mM HEPES and 2 mM ESTA). Cells were washed twice with assay medium and adjusted to 80,000 cells/mL. Approximately 100 μL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 μL transferred to triplicate microcultures followed by 50 μL assay medium for a final volume of 200 μL. After an additional 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallac BetaPlace β counter. Results in Table 4 below show the $IC_{50}$ for certain compounds of the present invention.

TABLE 4

| Compound (Example Reference) | $IC_{50}$ nM |
| --- | --- |
| 1 | 100 |
| 2 | 0.1 |
| 3 | 0.7 |
| 24 | Not active at the concentration tested |
| 27 | 1.0 |

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Test 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Test 4

A. Induction of fibroid tumors in guinea pig.

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice.

Tissue form human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri is harvested to assess the status of the organ.

Test 5

A. Tissue from human uterine fibroid tumors is harvested and maintained, in vitro, as primary nontransformed cultures.

Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Test 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 received intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Test 3

A. Surgical induction of endometriosis

Autographs of endometrial tissue are used to induce endometriosis in rats and/or rabbits. Female animals at reproductive maturity undergo bilateral oophorectomy, and estrogen is supplied oxogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of human endometrial tissue in nude mice.

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri is harvested to assess the status of the intact endometrium.

Test 4

A. Tissue from human endometrial lesions is harvested and maintained in vitro as primary nontransformed cultures.

Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

Inhibition of Aortal Smooth Cell Proliferation/Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant methods described in Ross, J. of *Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin. 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.1–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., *Exp. Cell Res.* 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above tests indicates that the compounds of the present invention are of potential in the treatment of restenosis.

The present invention also provides a method of alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5—2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such s quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation. The following formulation examples only are illustrative and are not intended to limit the scope of the present invention.

Formulations

In the formulations which follow, "active ingredient" means a compound of formula I, or a salt or solvate thereof.

| Formulation 1: Gelatin Capsules  Hard gelatin capsules are prepared using the following: | |
|---|---|
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

| Formulation 2: Tablets | |
|---|---|
| Ingredient | Quantity (mg/tablet) |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

| Formulation 3: Tablets | |
|---|---|
| Ingredient | Quantity (mg/tablet) |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

| Formulation 4: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

| Formulation 5: Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6: Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
|---|---|
| Ingredient | Quantity |
| Active ingredient | 50 mg |

| Ingredient | Quantity |
|---|---|
| *Formulation 7: Intravenous Solution* | |
| Isotonic saline | 1,000 mL |

The solution of the above ingredients is intravenously administered to a patient at a rate of about 1 mL per minute.

| Ingredient | Quantity (mg/capsule) |
|---|---|
| *Formulation 8: Combination Capsule I* | |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |
| *Formulation 9: Combination Capsule II* | |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |
| *Formulation 10: Combination Tablet* | |
| Active ingredient | 50 |
| Premarin | 1 |
| Corn Starch NF | 50 |
| Povidone, K29-32 | 6 |
| Avicel pH 101 | 41.50 |
| Avicel PH 102 | 136.50 |
| Crospovidone XL10 | 2.50 |
| Magnesium Stearate | 0.50 |
| Cab-O-Sil | 0.50 |

We claim:

1. A method for inhibiting aortal smooth muscle cell proliferation comprising administering to a human in need of such treatment an effective amount of a compound of

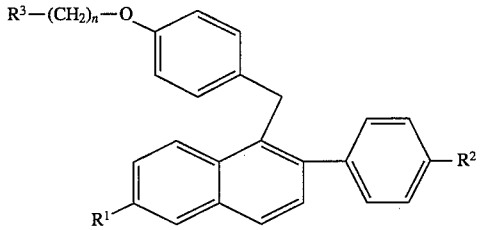

wherein $R^1$ is —H, —OH, —O($C_1$-$C_4$ alkyl), —OCO($C_1$-$C_6$ alkyl), or —OSO$_2$($C_4$-$C_6$ alkyl);

$R^2$ is —H, —OH, —O($C_1$-$C_4$ alkyl, —OCOC$_6$H$_5$, —OCO($C_1$-$C_6$ alkyl, or —OSO$_2$($C_4$-$C_6$ alkyl);

n is 2 or 3; and $R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

* * * * *

UNITED STATES PATENT AND TRADEMARK OFFICE
CERTIFICATE OF CORRECTION

PATENT NO. : 5,484,796

DATED : January 16, 1996

INVENTOR(S) : Henry U. Bryant, George J. Cullinan, Jeffrey A. Dodge, Kennan J. Fahey, Charles D. Jones, Charles W. Lugar, Brian S. Muehl It is certified that error appears in the above-indentified patent and that said Letters Patent is hereby corrected as shown below:

ON THE TITLE PAGE:

[75] Inventors:, line 2 reads …"Culliman…", should read --Cullinan--.

Column 6, line 13 reads …"$R^{1a}$ is -H…" should read --$R^{1b}$ is -H--

Column 6, line 14 reads …"$R^{2a}$ is -H"… should read --$R^{2b}$ is -H--

Column 9, line 62 reads …"$R^1-(CH_2)_n-Q$"… should read --$R^3-(CH_2)_n-Q$--

Column 13, line 29 reads …"$R^{1a}$, $R^{1a}$, and n"… should read --$R^{1a}$, $R^{2a}$, $R^{3a}$ and n--

Column 13, line 59 reads …"$R^2-(CH_2)_n-Q$"…ould read --$R^3-(CH_2)_n-Q$--

Column 14, line 7 reads …"$-C_6H_4-4'-C(C_1-C_4$ alkyl)"… should read -- $-C_6H_4-4'-0(C_1-C_4$ alkyl)--

Column 14, line 32 reads …"such as groups"… should read -such groups--.

Column 18, line 14 reads …"113.7, 133.6, 113.4"… should read ----113.7, 113.6, 113.4--

Column 18, line 38 reads …"To a solution of"… should read -- To a suspension of--

Column 18, line 43 reads …"overnight for 14 hours"… should read --for 14 hours --

UNITED STATES PATENT AND TRADEMARK OFFICE
CERTIFICATE OF CORRECTION

PATENT NO. : 5,484,796

DATED : January 16, 1996

INVENTOR(S) : Henry U. Bryant, George J. Cullinan, Jeffrey A. Dodge, Kennan J. Fahey, Charles D. Jones, Charles W. Lugar, Brian S. Muehl It is certified that error appears in the above-indentified patent and that said Letters Patent is hereby corrected as shown below:

Column 40, line 60 reads ..."6.56 (d, J=8.5 Hz," ... should read --7.56 (d, J=8.5 Hz,--

Column 40, line 61 reads ..."7.10-7.14"... should read --7.10-7.15--

Column 40, line 66 reads ..."C, 79.65; Y, 7.24"... should read --C, 79.65; H, 7.24--

Column 41, line 19 reads ..."6-methoxynaphthalenlyl"... should read --6-methoxynaphthalenyl--

Column 42, line 61 reads ..."otherwise stated, s a suspension"... should read --otherwise stated, as a suspension--

Column 46, line 11 reads ..."2 mM ESTA"... should read --2 mM EDTA--

Column 48, line 36 reads ..."supplied oxogenously thus"... should read --supplied exogenously thus--

Column 54, line 11 reads ..."of a compound of"... should read -- of a compound of formula I--

UNITED STATES PATENT AND TRADEMARK OFFICE
CERTIFICATE OF CORRECTION

PATENT NO. : 5,484,796

DATED : January 16, 1996

INVENTOR(S) : Henry U. Bryant, George J. Cullinan, Jeffrey A. Dodge, Kennan J. Fahey, Charles D. Jones, Charles W. Lugar, Brian S. Muehl It is certified that error appears in the above-indentified patent and that said Letters Patent is hereby corrected as shown below:

Column 18, line 51 reads ..."(23.6 g, 27.4 mmol)"... should read -- (23.6 g. 47.2 mmol) --

Column 18, line 64 reads ..."4H) 3.90-2.99"... should read --4H) 2.90-2.99--

Column 18, line 67 reads ..."7.18; N, 266." Should read --7.10; N, 2.66.--

Column 21, line 6, reads ..."cm$^{JTT}$; should read --cm$^{-1}$;--

Column 23, line 17 reads ..."on hexanes,"... should read --in hexanes,--

Column 25, lines 19-23 are blank, should read --

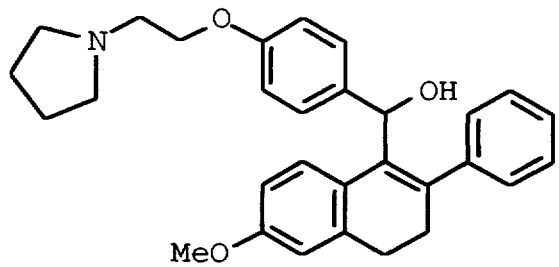

UNITED STATES PATENT AND TRADEMARK OFFICE
CERTIFICATE OF CORRECTION

PATENT NO. : 5,484,796
DATED : January 16, 1996          Page 4 of 5
INVENTOR(S) : Henry U. Bryant, George J. Cullinan, Jeffrey A. Dodge, Kennan J. Fahey, Charles D. Jones, Charles W. Lugar, Brian S. Muehl It is certified that error appears in the above-indentified patent and that said Letters Patent is hereby corrected as shown below:

Column 26, line 27 reads ..."H, 6.35; N, 2.32"... should read --H, 6.85; N, 2.82--

Column 27, line 55, reads ..."After 13"... should read --After 18--

Column 28, line 15 reads ..."3,5-dihydronaphth-1-yl"... should read --3,4-dihydronaphth-1-yl--

Column 30, line 55 reads ..."(1.62 g, 260"... should read --(1.61 g, 2.60 --

Column 33, the structure on lines 42-54 should be removed and the following structure inserted:

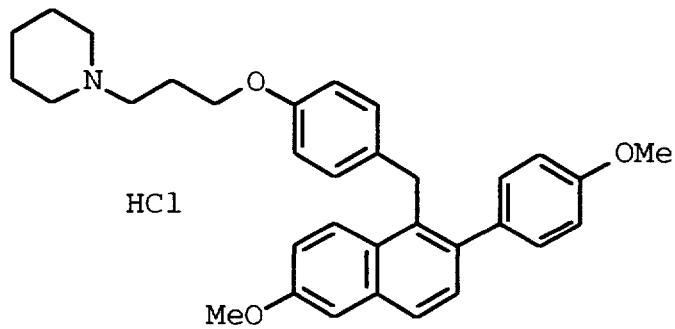

Column 36, line 34 reads ..."64.42, 55.20, 55.13"... should read --62.42, 55.20, 55.13--

UNITED STATES PATENT AND TRADEMARK OFFICE
CERTIFICATE OF CORRECTION

PATENT NO. : 5,484,796
DATED : January 16, 1996
INVENTOR(S) : Henry U. Bryant, George J. Cullinan, Jeffrey A. Dodge, Kennan J. Fahey, Charles D. Jones, Charles W. Lugar, Brian S. Muehl It is certified that error appears in the above-indentified patent and that said Letters Patent is hereby corrected as shown below:

Column 54, line 25 reads ..."—O ($C_1$-$C_4$ alkyl) -OCO ($_1$-$C_6$ alkyl)"...
should read ---O ($C_1$-$C_4$ alkyl, -OCOC$_6$H$_5$, -OCO ($_1$-$C_6$ alkyl)

Signed and Sealed this

Twenty-eighth Day of October, 1997

Attest:

BRUCE LEHMAN

Attesting Officer

Commissioner of Patents and Trademarks